United States Patent [19]
Yacynych et al.

[11] Patent Number: 5,286,364
[45] Date of Patent: Feb. 15, 1994

[54] SURFACE-MODIFIED ELECTOCHEMICAL BIOSENSOR

[75] Inventors: Alexander M. Yacynych, East Brunswick; Sylvia S. Piznik, Jackson; Eugene R. Reynolds, Highland Park; Robert J. Geise, Piscataway, all of N.J.

[73] Assignee: Rutgers University, New Brunswick, N.J.

[21] Appl. No.: 677,384

[22] Filed: Mar. 29, 1991

Related U.S. Application Data

[63] Continuation-in-part of Ser. No. 456,075, Dec. 20, 1989, which is a continuation of Ser. No. 59,706, Jun. 8, 1987, abandoned.

[51] Int. Cl.$^5$ ............................................. G01N 27/26
[52] U.S. Cl. .................................... 204/418; 205/198; 205/317; 204/403; 435/817
[58] Field of Search ............... 204/78, 418, 59 R, 403; 205/317, 198; 435/817

[56] References Cited

U.S. PATENT DOCUMENTS

4,636,430  1/1987  Moehwald ............................ 204/78
5,133,856  7/1992  Yamaguchi et al. ................. 204/418

OTHER PUBLICATIONS

Peter T. Kissinger and William R. Heineman, Ed., *Laboratory Techniques in Electroanalytical Chemistry*, pp. 45-49.

You, X.-Z.; Ding, Z.-F.; Peng, X.; Xue, G.; "(2-Formyl-1-Chlorovinyl) Ferrocene Film Electrode Prepared by Electrochemical Polymerization," Electrochimica Acta, 34(2), 1989, pp. 249-253.

Philippe Mourcel, et al., "Depositing Organic Polymers on Steel by Electropolymerizataion: Their Growth Mechanism and Passivating Nature," *J. Electroanal. Chem.*, 145 (1983), pp. 467-472.

Pham, M. C.; Hachemi, A.; DuBois, J. E.; "An Apparently Totally Electroactive Film Obtained by Electropolymerizing 5-Hydroxy-1,4-Naphthoquinone Outs Graphite" *J. Electroanal. Chem.* 161 (1984) pp. 199-204.

Pham, M. C.; Hachemi, A.; Delamar, M.; "XPS Structure Elucidation of Polymer Film Coatings Obtained by Elelctropolymerizing Naphthol Derivatives," *J. Electroanal. Chem.* 184 (1985) pp. 197-203.

Robert J. Waltman and A. F. Diaz, "The Electrochemical Oxidation and Polymerization of Polycyclic Hydrocarbons," *J. Electrochem. Soc.: Electrochemical Science and Technology*, Mar. 1985, pp. 631-634.

(List continued on next page.)

Primary Examiner—John Niebling
Assistant Examiner—Bruce Bell
Attorney, Agent, or Firm—Peter K. Trzyna; Richard A. Speer

[57] ABSTRACT

An electrode for a biosensor (e.g., a glucose biosensor) has a layer of an electrically insulating polymer formed in situ on its operating surface by electropolymerization. For example, a diaminobenzene and a dihydroxybenzene (e.g., 1,3-diaminobenzene and resorcinol) are copolymerized on the electrode's surface by immersing the electrode in a circulating dilute solution of the monomers in deaerated phosphate buffer, and applying a small, continuously cycling voltage between that electrode and another electrode (e.g., from 0.00 V to 0.80 V) until current flow between the electrodes decreases to a minimum. Because the polymer is electrically insulating, polymerization ceases while the polymer layer is still very thin (e.g., 10 nm). An analyte sensing agent, e.g., an enzyme such as immobilized glucose oxidase, is imbedded in the polymer, but with a number of its analyte recognition sites unblocked. The polymer layer shields the electrode surface from interferrents and fouling agents such as uric acid and proteins, but it is sufficiently porous to permit smaller electroactive molecules (e.g., hydrogen peroxide) generated through contact of the enzyme with the analyte molecules to diffuse through to the electrode surface. Preferably a ferrocene compound (e.g., alpha-hydroxy-ethylferrocene or 1,1'-dimethylferrocene), which functions as an electron mediator, is applied to the polymer film, and held there by adsorption.

11 Claims, 24 Drawing Sheets

OTHER PUBLICATIONS

DuBois, J. E., Lacaze, P.-C.; Pham, M. C.; "Obtaining Thin Films of 'Reactive Polymers' on Metal Surfaces by Electrochemical Polymerization." Part III. Amino Substituted Polyphenylene Oxide Films. Application to Preparation of Ferrocene Electroactive Films. *J. Electroanal. Chem.*, 117 (1981), pp. 233-241.

Delamar, M.; Chehimi, M.; DuBois, J.-E.; "XPS Study of the Growth of an Electropolymerized Thin Film," *J. Electroanal. Chem.*, 169 (1984), pp. 145-156.

Eugene R. Reynolds, David P. Raite, Alexander M. Yacynych, "Miniaturized Electrochemical Biosensors and Glucose" Oral presentation at 1989 MARM–cover of abstract book enclosed.

Nicola C. Foulds and Christopher R. Lowe, "Immobilization of Glucose Oxidase in Ferrocene-Modified Pyrrole Polymers," *Anal. Chem.*, 1988, pp. 2473-2478.

Anthony E. G. Cass, Graham Davis, Graeme D. Francis and H. Allen O. Hill, "Ferrocene-Mediated Enzyme Electrode for Amperometric Determination of Glucose," *Anal. Chem.*, 1984, 56, pp. 667-671.

Brian A. Gregg and Adam Heller, "Cross-Linked Redox Gels Containing Glucose Oxidase for Amperometric Biosensor Applications," *Anal. Chem.*, 1990, 62, pp. 258-263.

G. Jonson, L. Gorton and L. Pettersson, "Mediated Electron Transfer from Glucose Oxidase at a Ferrocene-Modified Graphite Electrode," 1988, pp. 49-55.

M. F. Suaud-Chagny and F. G. Gonon, "Immobilization of Lactate Dehydrogenase on a Pyrolytic Carbon Fiber Microelectrode," *Anal. Chem.*, 1986, 58, pp. 412-415.

Joseph Wang, Ruiliang Li and Meng-Shan Lin, "Flow Cell Based on Glucose Oxidase-Modified Carton Fiber Ultramicroelectrode," *Electroanalysis*, 1, 1989, pp. 151-154.

Yoshihito Ikariyama, Shigeru Yamuchi, Tomoaki Yukiashi, and Hiroo Ushioda, "Micro-Enzyme Electrode Prepared on Platinized Platinum", *Analytical Letters*, 20(9), 1987, pp. 1407-1416.

Yoshihito Ikariyama, et al., "One Step Fabrication of Microbiosensor Prepared by the Codeposition of Enzyme and Platinum Particles," *Analytical Letters*, 20(11), 1987, pp. 1791-1801.

Yoshito Ikariyama, et al., "Surface Control of platinized platinum as a transducer matrix for micro-enzyme electrodes," *J. Electroanal. Chem.*, 251, 1988, pp. 267-274.

Yoshihito Ikariyama, et al., "High Performance Micro-Enzyme Sensor Using Platinized Microelectrode," *Bull. Chem. Soc. Jpn.*, 61, 1988, pp. 3525-3530.

Yoshihito Ikariyama et al., "Electrochemical Fabrication of Amperometric Microenzyme Sensor," *J. Electrochem. Soc.*, vol. 136, No. 3, Mar. 1989, pp. 702-706.

J. Y. Kim and Y. H. Lee, "Fast Response Glucose Microprobe," *Biotechnology and Bioengineering*, vol. 31, 1988, pp. 755-758.

RESPONSE OF A PLATINIZED CARBON ULTRAMICROBIOSENSOR (W/O FILM) TO INTERFERENCES AND GLUCOSE AT E = +0.70 V VS. Ag/AgCl

A. 0.44 mM URIC ACID
B. 0.21 mM ACETAMINOPHEN
C. 0.11 mM ASCORBIC ACID
D. 5.00 mM GLUCOSE

A. 0.44 mM URIC ACID
B. 0.21 mM ACETAMINOPHEN
C. 0.11 mM ASCORBIC ACID
D. 5.00 mM GLUCOSE

RESPONSE OF A PLATINIZED CARBON ULTRAMICROBIOSENSOR WITH 1,3-DAB +RES. FILM TO INTERFERENCES AND GLUCOSE AT E = +0.70 V VS. Ag/AgCl

SURFACE-MODIFIED ELECTOCHEMICAL BIOSENSOR

This application is a continuation-in-part of Ser. No. 07/456,075 (Yacynych and Sasso), filed Dec. 20, 1989, which, in turn, was a continuation of Serial No. 07/059,706 (Yacynych and Sasso), filed Jun. 8, 1987 (now abandoned).

BACKGROUND OF THE INVENTION

The present invention relates to chemically modified electrodes for use as biosensors, such as have been applied in clinical chemistry testing and in other monitoring and control environments, and is more particularly directed to problems relating to electrode fouling and interference from other species present in complex matrices such as blood, serum, or fermentation broths.

Biosensors are devices for sensing such substances as electrolytes, gases, proteins, enzymes, metabolites, antibodies, and antigens. They find wide application in such diverse fields as clinical chemistry testing, bioreactor monitoring and control, fermentation control, and medical research.

A biosensor of the sort of interest here generally includes a base electrode and a biochemically discriminating element disposed about the electrode. Typically the biochemically discriminating element is provided by a membrane which surrounds the electrode. The biosensor is placed in contact with the sample substrate under investigation, and the membrane isolates and transforms the desired analyte into an electrically active species or otherwise generates an electrical potential, which is sensed and monitored by the base electrode. Familiar examples include the use of a glass membrane, which selects and traps the desired electrolyte cation, such as $Na^+$, in the silicate matrix of the glass, thereby producing a charge separation which is sensed by the electrode, and the use of a polyvinyl chloride matrix incorporating the antibiotic molecule valinomycin for selectively extracting $K^+$ ions.

Other examples of biosensors are provided by so-called enzyme electrodes, in which the membrane is provided by a composite containing one or more immobilized enzymes. The enzymes catalyze a reaction of the sample substrate to consume or to generate a redox-active species in an amount related to the concentration of the target analyte in the sample substrate. The redox-active species may then be detected by measuring current flow at the electrode mediated by the redox-active species. The development of other membranes for selectively discriminating and sensing other analytes is currently an area of active research.

Paralleling the development of new membranes is the development of improved base electrodes. One such development is the use of reticulated vitreous carbon (IIRVCII) as a base electrode. See, for example, the work of Wieck, Heider, and Yacynych, reported in *Anal. Chem. Acta*, Vol. 158, pp. 137 et sea. (1984), in which an RVC electrode is incorporated into an immobilized enzyme detector for a flow injection determination of glucose. RVC presents a complex microenvironment to the substances to be detected by the base electrode. Attempts have been made to modify the microenvironment for improved electrode performance. See, for example, the work of Will and Iacovangelo, appearing in the *Journal of the Electrochemical Society*, Vol. 131, pp. 590 et secf. (1984), which discloses the electrodeposition of zinc metal onto RVC surfaces for improved performance.

Notwithstanding progress in the development of new sensing agents and electrodes, biosensors—old and new—fail to achieve their theoretical peak performance because of interference of species other than the desired analyte which can contribute to the potential difference or to the current sensed by the base electrode, thereby compromising the selectivity or measurement precision of the biosensor, and because of the fouling of the base electrode with repeated use.

SUMMARY OF THE INVENTION

The present invention provides a biosensor having an improved microenvironment which reduces fouling of the base electrode and which reduces the effects of interferents in the sample under examination.

Briefly, a biosensor according to the invention is comprised of a base electrode and a composite sensing layer, which, in turn, comprises an analyte-sensing agent combined with a polymerized film. The characteristics of the polymerized film and the structure of the composite layer are such as to protect the biosensor against fouling with repeated use and to shield the base electrode from interferents which otherwise would tend to reduce the capability of the biosensor to distinguish the target analyte. The film has an effective porosity which is smaller than the characteristic sizes of the fouling agents and interferents expected in the sample under investigation. The film generally is not permeable to molecules as large as the monomer of which the polymer is formed, but is permeable to molecules as small as hydrogen peroxide. one such film found to be generally effective in the environments described below is formed of a diaminobenzene, preferably copolymerized with a dihydroxybenzene.

In the composite sensing layer the film is disposed so as not to interfere with the active sites of the sensing agent which are responsible for detecting the target analyte. The sensing agent may be disposed directly on the base electrode first, and the film then disposed on and about the sensing agent. Alternatively, the film may be disposed directly on the base electrode first, and then the sensing agent disposed on the film.

It is an advantage of the invention that the composite layer may be formed exceedingly thin. The sensing agent, which generally includes a basic functional unit, may be only one such functional unit thick in the composite layer, and the polymer film may likewise be only a single monomer unit thick. With such a thin composite layer the diffusion time through the layer is greatly reduced, thereby reducing the response time and recovery time of the biosensor.

A further appreciation and understanding of the invention and its advantages will be gained by reference to the following portions of the specification and the drawings.

DETAILED DESCRIPTION OF A PREFERRED EMBODIMENT

Figure 1A:
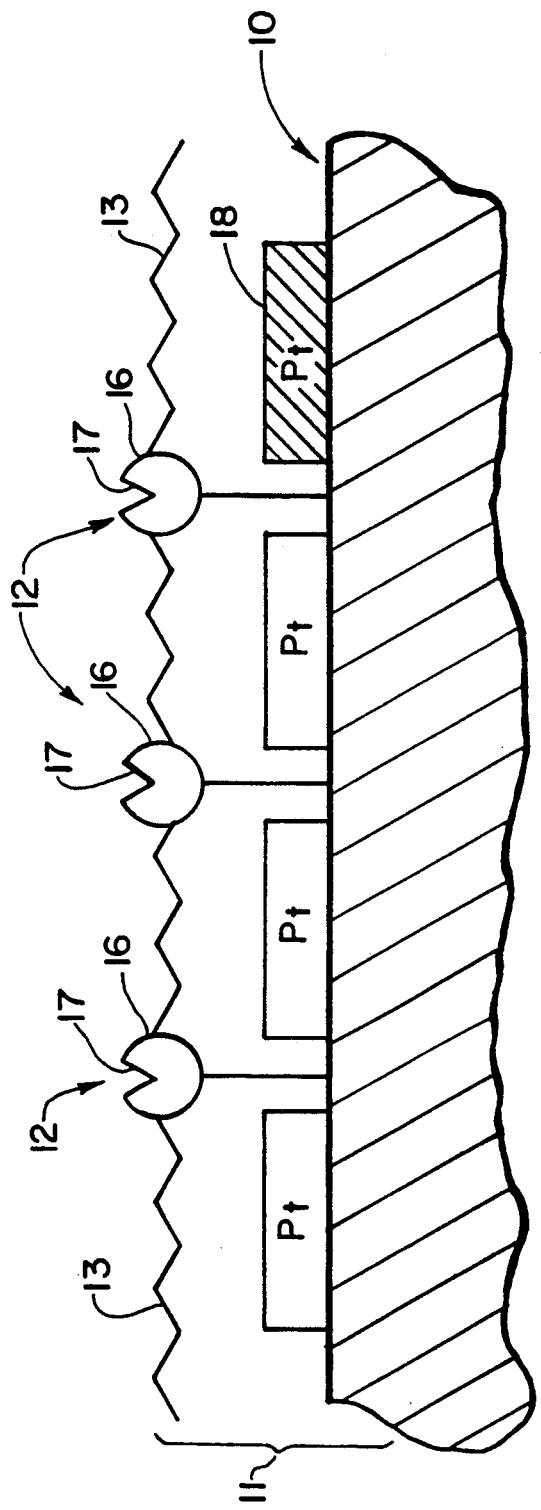
FIG. 1a shows a schematic representation of an enlarged cross-sectional side view of a segment of the contact surface of an idealized sensor according to the invention.

FIG. 1a shows an idealized representation of the operative portion of a biosensor in an embodiment of the present invention. The biosensor includes a base electrode 10 and a composite layer 11 which is disposed on the base electrode. The composite layer, in turn, includes an analyte-sensing agent 12 and a polymer film 13, which has certain characteristics described more fully below which enable the film to serve as a shield against interferents and fouling agents without significantly diminishing the analyte-sensing capability of the agent 12.

As a specific illustration, a biosensor according to the invention is described herein for use with physiological samples and in particular for sensing the presence and concentration of glucose within a physiological sample. Those skilled in the art will appreciate that the methods and structures illustrated below are also applicable to the sensing of substances other than glucose and samples other than physiological ones.

In biosensors generally, the analyte-sensing agent may be provided by a variety of substances. Enzymes, antibodies, antigens, electrolyte-specific lattices such as glass, and bimolecular receptors are familiar examples. These agents provide recognition sites for a particular substance found in the sample under test, for example, the active sites on an enzyme or the negatively charged oxygen atoms in the silicate matrix of a glass membrane. In the schematic representation of FIG. 1a the agent 12 is depicted as an enzyme 16 with active site 17. Enzymes are complex proteins that are produced by living cells. They catalyze specific biochemical reactions. Glucose oxidase, for example, catalyzes the conversion of glucose to gluconic acid. The prosthetic group of this enzyme, flavine adenine dinucleotide (FAD), (of which there are two per molecule) oxidizes the substrate glucose, and is thus converted to a reduced form ($FADH_2$) Oxygen in the biological sample then oxidizes the $FADH_2$ back to FAD to recycle the enzyme. Hydrogen peroxide is produced from the reduction of oxygen when it oxidizes $FADH_2$. In an amperometric glucose biosensor the electrode is held at a sufficiently anodic potential (e.g., +0.58 volt vs. a silver/silver chloride reference electrode) to oxidize the hydrogen peroxide, and the current produced is proportional to the concentration of glucose. This electrochemical reaction also recycles some of the oxygen. (Another portion of the oxygen is lost by diffusion into the biological sample, which is an aqueous solution.)

Figure 1B:
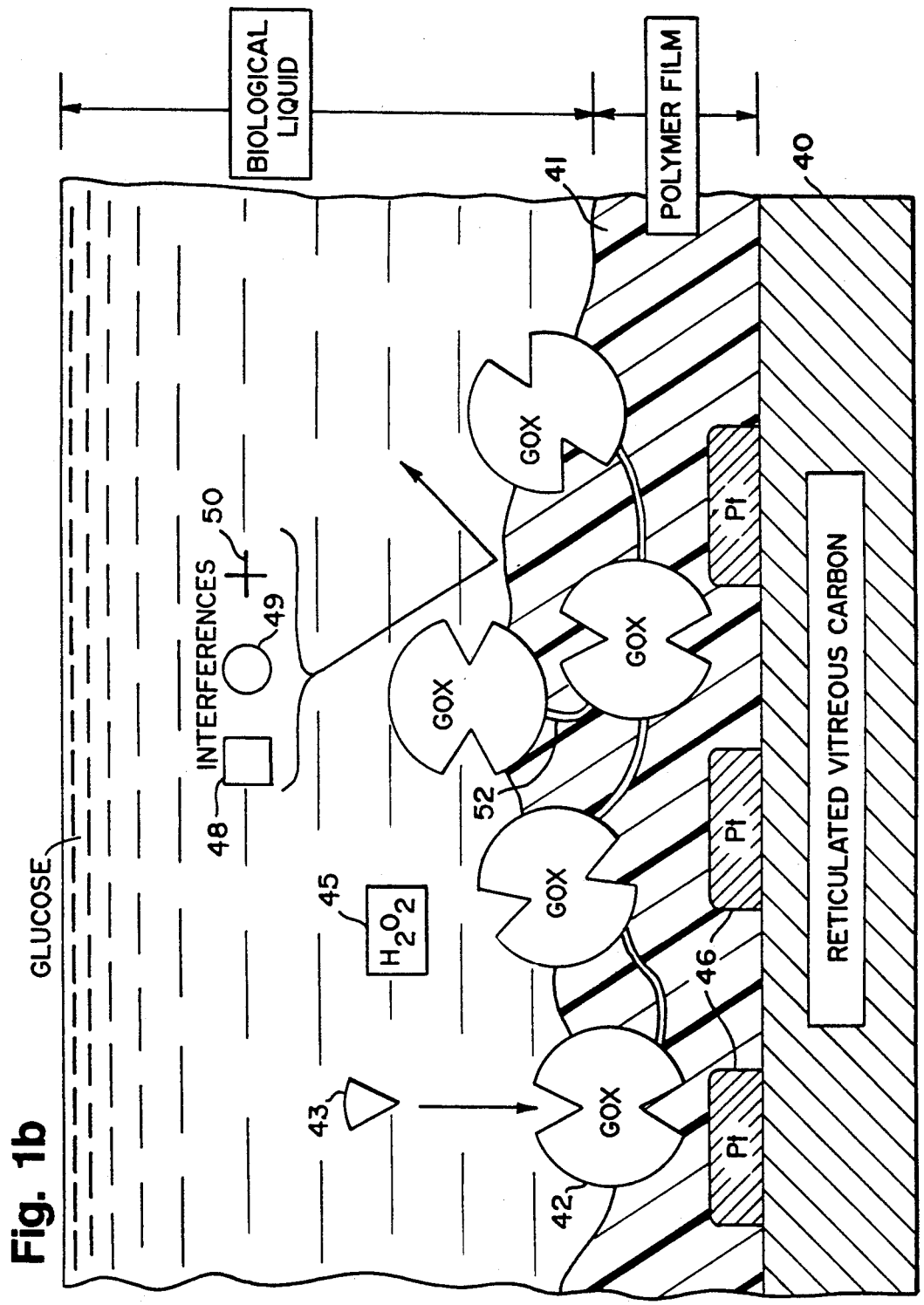
FIG. 1b is a second schematic representation, similar to FIG. 1a, of a portion of the contact surface of a glucose biosensor of the present invention.

The enzyme is depicted in FIG. 1a as being linked directly to the electrode surface (e.g., by carbodiimide attachment); however, the enzyme may also be cross-linked (e.g., by glutaraldehyde crosslinking) without direct linking to the surface, as shown in FIG. 1b.

Other types of immobilization techniques include the use of cyanogen bromide, which links the sensing agent to vicinal hydroxyl groups on the surface of the electrode; cyanuric chloride, which attaches through hydroxyl or amine functional groups; and attachments through hydrophilic linkages, such as a biotin/avidin/biotin system. The advantages of the biotin/avidin immobilization are that the binding is very strong and that the sensing agent can be easily replaced without further modification of the electrode surface. These techniques, as well as others that could be used successfully, are known to those skilled in the art of immobilization of sensing agents, and chemical modification of surfaces.

In typical operation, when an enzyme is employed, the enzyme catalyzes a reaction with the analyte, either to form electroactive products, such as hydrogen peroxide, or to consume electroactive reactants, such as oxygen. These intermediate substances, referred to herein as intermediate "reactants" can then be detected amperometrically at the base electrode by well known techniques. Although idealized in FIG. 1a as a single enzyme, the analyte-sensing agent may also be provided by a composite structure containing several immobilized enzymes as well as by immunological agents, such as antibodies, antigens, or haptens, as well as the common electrolyte-responsive agents.

Conventional biosensors face the serious problems of electrode fouling, which diminishes the ability of the electrode to respond appropriately, and of interference from undesired substances in the sample, which also produces interfering electrical signals in the electrode. Some conventional enzyme electrodes, for example, imbed the enzyme structure in a macroscopic, self-supporting membrane to overcome these problems. Others provide additional membrane layers above and below the enzyme layer to filter out the interferents and fouling agents. Although these systems have been commercially developed, they face a number of limitations, such as their thickness. If the diameter of a glucose oxidase molecule (ca. 8.5 nm) is considered a basic operational unit, then the self-supporting enzyme membranes are generally at least 100 basic operational units thick and are typically several hundred such units thick. Anti-fouling or anti-interference layers add to the overall thickness. The thick membranes result in a slow and complex diffusion path for the analyte to reach the enzyme and/or for the intermediate reactants to reach the electrode. Slow diffusion time, of course, adversely affects the response time, recovery time, and sampling rate of the biosensor. The thick-membrane construction technique is also limited to electrodes presenting substantially planar two-dimensional surfaces. Moreover, for sensors having complex and slow diffusion paths, the diffusion rates must remain relatively constant for the biosensor to be calibrated and to maintain that calibration.

Compared with the discrete, thick-membrane construction previously employed, the present technique provides a thin sensing layer showing excellent resistance to fouling and interferents and presenting a substantially shorter diffusion path. In the present biosensor the analyte-sensing agent need be no thicker than several tens of the basic operational units forming the agent, and generally may be much thinner. For example, when the sensing agent is an immobilized enzyme, it may be as little as one such unit thick for an enzyme linked directly to the electrode surface, or several units thick for a crosslinked enzyme. The anti-fouling polymer film of the present invention need be no thicker than the sensing agent and in general may be as thin as only several of the monomer units of which the polymer is composed. The overall thickness of the composite layer, comprised of sensing agent and polymer film, may thus be kept small—on the order of molecular dimensions as opposed to the dimensions of typical discrete membranes.

Figure 2:
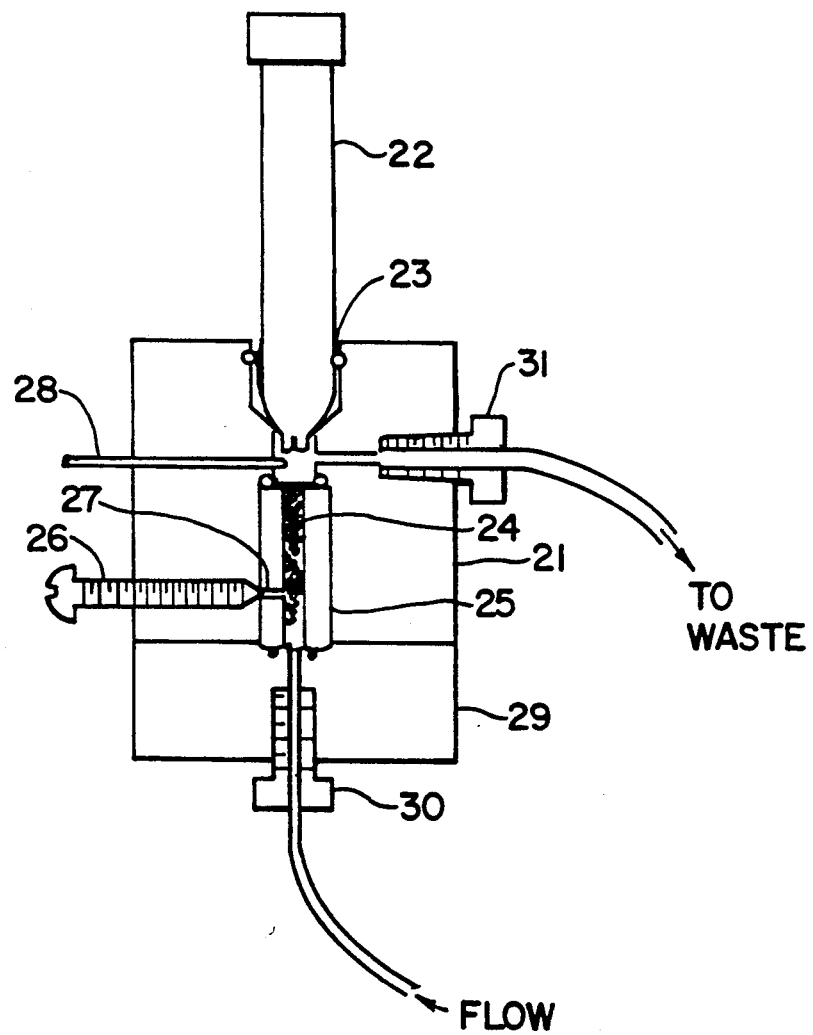
FIG. 2 is a cross-sectional view of an electrochemical flow cell for use in forming and testing a biosensor according to the invention.
Figure 3:
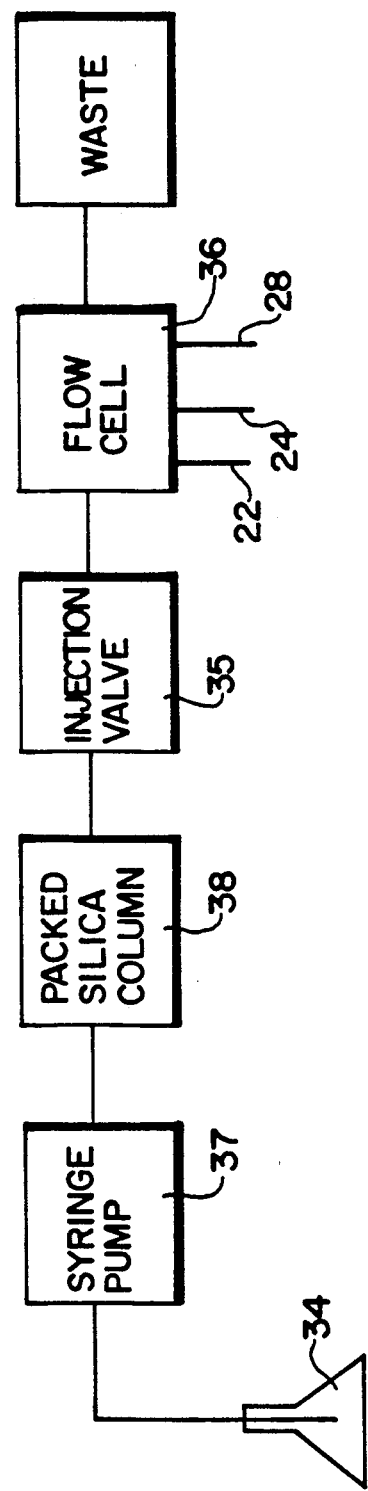
FIG. 3 is block diagram of a flow injection analysis system including the flow cell of FIG. 2.

A biosensor according to the present invention was prepared and tested using the flow cell design shown in FIG. 2, which was included in the flow injection analysis (FIA) system of FIG. 3. The flow cell includes a body 21 formed of a plexiglass rod roughly 4.5 cm in length. A reference electrode 22 is secured in the top of the body 21, sealed by O-ring 23. The reference electrode was provided by a saturated calomel electrode (SCE) or by a Ross reference electrode (RRE). The RVC working electrode 24 is contained within a central bore in a plexiglass rod or cartridge 25, which is 9.5 mm in diameter. Electrical contact with the RVC is established by brass screw 26 and graphite "pencil lead" 27. The pencil lead was electrically secured to the RVC with epoxy resin filled with conducting graphite. A platinum wire auxiliary electrode 28 extends through the body to a position between the reference and working electrodes. The RVC cartridge 25 is held within the body 21 by a lower body portion 29, which is removable for changing the cartridge. The lower body portion 29 is tapped to receive inlet 30 for the carrier stream. The stream exits the cell at outlet 31.

For preparing and testing the biosensor, a sample solution 34 is introduced by an injection valve 35 into the carrier stream entering the flow cell 36 and the solution is circulated through the flow cell by a syringe pump 37. With the flow cell of FIG. 2 an injection valve was employed having a 5 $\mu$l or 100 $\mu$l sample loop. Since the RVC electrode 24 does not impose any back pressure on the syringe pump, a packed silica column 38 was interposed between the pump 37 and injection valve 35 to increase the back pressure and eliminate the slight pulsing of the pump, thereby improving the reproducibility of the flow rate through the system.

All electrochemical tests were performed using either a PARC model 364 or 264A polargraphic analyzer available from Princeton Applied Research of Princeton, N.J. All potentials are referenced to a Ross reference electrode (RRE) or a standard saturated calomel electrode (SCE). A Rabbit peristaltic pump available from Rainin Instruments, of Woburn, Mass., was used to circulate the solution of monomer(s), through the RVC electrode 24 during electropolymerization, and also to circulate the solution of enzyme during immobilization, as described more fully below. Temperature studies were performed in a water bath thermostatted using a lauda constant temperature immersion circulator, Model MT, available from Fisher Scientific Supply of Springfield, N.J. A DuPont Instruments model 870 HPLC pump, available from DuPont Co. of Wilmington, Del., was used for the flow injection analysis.

The biosensor embodiment illustrated in FIG. 1a employs a base electrode 10 of reticulated vitreous carbon which presents a complex irregular surface extending throughout a three-dimensional domain. The RVC electrode may be prepared as described by H. Wieck, C. Skien, and A. Yacynych in *Anal. Chim. Acta*, Vol. 142, pp. 277, et seq. (1982) and by H. Wieck, G. Heider and A. Yacynych in *Anal. Chim. Act.*, Vol. 158, pp. 137 et secf. (1984). See also G. Heider, Ph.D. Dissertation, Rutgers, The State University of New Jersey, Brunswick, N.J. (1984). Formed in this manner, the electrode presents an enhanced operative surface area per unit volume of electrode. other conducting materials, familiar from known biosensors, may of course also be used for the electrode. Such other materials include other carbonaceous materials like pyrolytic graphite or glassy carbon, as well as metals or metals coated with metal oxide layers, conducting salts, conducting polymers, and semiconductors.

When an enzyme is to be immobilized on the surface, it is sometimes advantageous to employ a partially platinized RVC electrode, although this is not necessary for operation of the invention. Electrodeposition of platinum onto the RVC surface is carried out similarly to electrodeposition of zinc on RVC as described by F. Will and C. Iacovangelo in *J. Electrochem. Soc.*, pp. 590 et sea. (1984). For example, the electrodeposition may be carried out by circulating a platinate solution through the flow cell of FIG. 2 with the reference port plugged and using the remaining two electrodes for galvanostatic deposition onto the RVC surface.

In the embodiment illustrated in FIG. 1a the sensing agent is provided by glucose oxidase immobilized on the RVC surface. The glucose oxidase may be immobilized by known attachment schemes such as glutaraldehyde crosslinking or by direct carbodiimide attachment to carbonaceous sites on the electrode surface. See the article by Wieck, Heider and Yacynych, supra.

The polymer film 13 protects the sensing agent and base electrode against fouling and provides a permselective barrier to prevent interferents from reaching the electrode. In the illustrative example presented here, the polymer film is provided by 1,2-diaminobenzene which is electropolymerized onto the RVC surface. Other diaminobenzenes or copolymers of diaminobenzenes will also serve this function as well; and it is expected that other aromatic amines, phenols, or sulfur-containing aromatic compounds may also be electropolymerized to prepare operable films. Preferably, the monomer will be difunctional as regards amine and-/or hydroxyl groups—i.e., it will have substituted on the aromatic ring either two amino groups, two hydroxyl groups, or one of each.

To form the polymer film, 1,2-diaminobenzene of 98% purity was further purified by recrystallizing from dichloromethane three times, using standard techniques, and was decolorized with activated carbon (2 g/L) during the first recrystallization. The final product had white platelike crystals with a melting point range of 100.8°-102.0° C.

A solution of 1,2-diaminobenzene (3 Mm in 0.1M, pH 6.5, potassium phosphate buffer) was deaerated for 0.5 h with high purity grade nitrogen prior to use, and a nitrogen atmosphere was maintained over the solution during the course of the experiment. The platinized RVC electrode 24, with the glucose oxidase immoblized on its surface, was inserted into the cell, which was connected to a Rabbit peristaltic pump. The solution was circulated at a flow rate of 0.8 ml/min throughout the electropolymerization process. Cyclic voltammetry was used for both film formation and to follow its progress on the electrode surface. Cyclic voltammetric scans were obtained by cycling from 0.0 V to +0.8 V vs SCE, using the platinized RVC electrode 24 as the working electrode and platinum 28 as the auxiliary electrode, at a scan rate of 2 my/s, until the current decreased to a minimum. A constant potential of 0.8 V can also be used, but by cycling the potential a more robust film is produced.

The 1,2-diaminobenzene was thereby homopolymerized directly onto the platinized surface of the RVC electrode to form a polymer having the following structural formula:

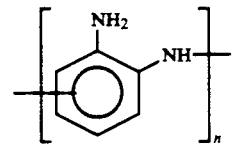

Because poly (1,2-diaminobenzene) is electrically insulating, once the polymer layer got to an average thickness of approximately 10 nm, current flow from the auxiliary electrode to the RVC working electrode dropped to an ineffective amperage, and the polymerization automatically ceased. The polymer film had an effective porosity smaller than the characteristic minimum size of the fouling agents and interferents commonly found in human serum, e.g., L-ascorbic acid, L-cysteine, uric acid, proteins, and acetaminophen. In other words, the film was sufficiently solid to shield the electrode surface from such compounds. The polymer layer had some porosity, however, and it was sufficient to allow hydrogen peroxide (the electroactive molecule generated by the conversion of glucose to gluconic acid) to diffuse through and contact the electrode surface.

Once the polymer was coated on the electrode, the cell was transferred to the flow injection analysis system for testing.

Electropolymerization with an electrically insulating film such as 1,2-diaminobenzene is advantageous, in that the thickness of the resulting film is self-regulating and maintained fairly thin, e.g., in the range of about 5 to 15 nm. As the insulating film is deposited, the electropolymerization process comes to a stop due to the insulating characteristic of the deposited film.

FIG. 1b uses a slightly different representational style than FIG. 1a to illustrate a segment of the surface of the sensing element of a glucose biosensor of the present invention. As shown in FIG. 1b, electrode 40 is made of reticulated vitreous carbon which has been platinized. overlaying the surface of electrode 40 is a thin film of polymer 41 that has been formed in situ by electropolymerization of electropolymerizable monomer. Embedded in the polymer film 41 are molecules of glucose oxidase (GOX) 42, which are linked together by units of glutaraldehyde 52. Some of the GOX molecules 42 are partly exposed, so that glucose molecules 43 in the liquid 47 being analyzed can contact the unblocked recognition sites 44 in the GOX molecules. The thickness of polymer layer 41 varies somewhat, but, as indicated, it is far less than 100 times the thickness of a basic operational unit of the glucose oxidase 42, i.e., less than 850 nm.

When contact between glucose molecule 43, and recognition site 44 is made, the glucose oxidase catalyzes the oxidation of glucose, which causes a molecule of hydrogen peroxide 45 to be formed. Polymer film 41 is sufficiently porous that the hydrogen peroxide molecule 45 can diffuse through it and reach the platinum sites 46 on the electrode surface. This causes the electrochemical oxidation of hydrogen peroxide, producing an electric current which is proportional in amperage to the concentration of glucose in the sample. Molecules of potential interferents such as uric acid 48, L-ascorbic acid 49, and L-cysteine 50 (all shown symbolically) will not permeate the polymer film 41 to any significant decree, however, due to their being larger than the effective porosity of the polymer.

Permselectivity Characteristics of Electropolymerized 1,2-Diaminobenzene

As is known, the major interferents in blood serum are uric acid, acetominophen, L-ascorbic acid, and L-cysteine. See, for example, Yao, T. Anal. Chim. Acta., Vol. 153 (1983), pp. 175–180. Their approximate concentration in human serum is: uric acid, 0.29 mill; acetominophen, 0.21 Mm; L-ascorbic acid, 0.06 mill; and L-cysteine, 0.175 Mm.

Figure 4:
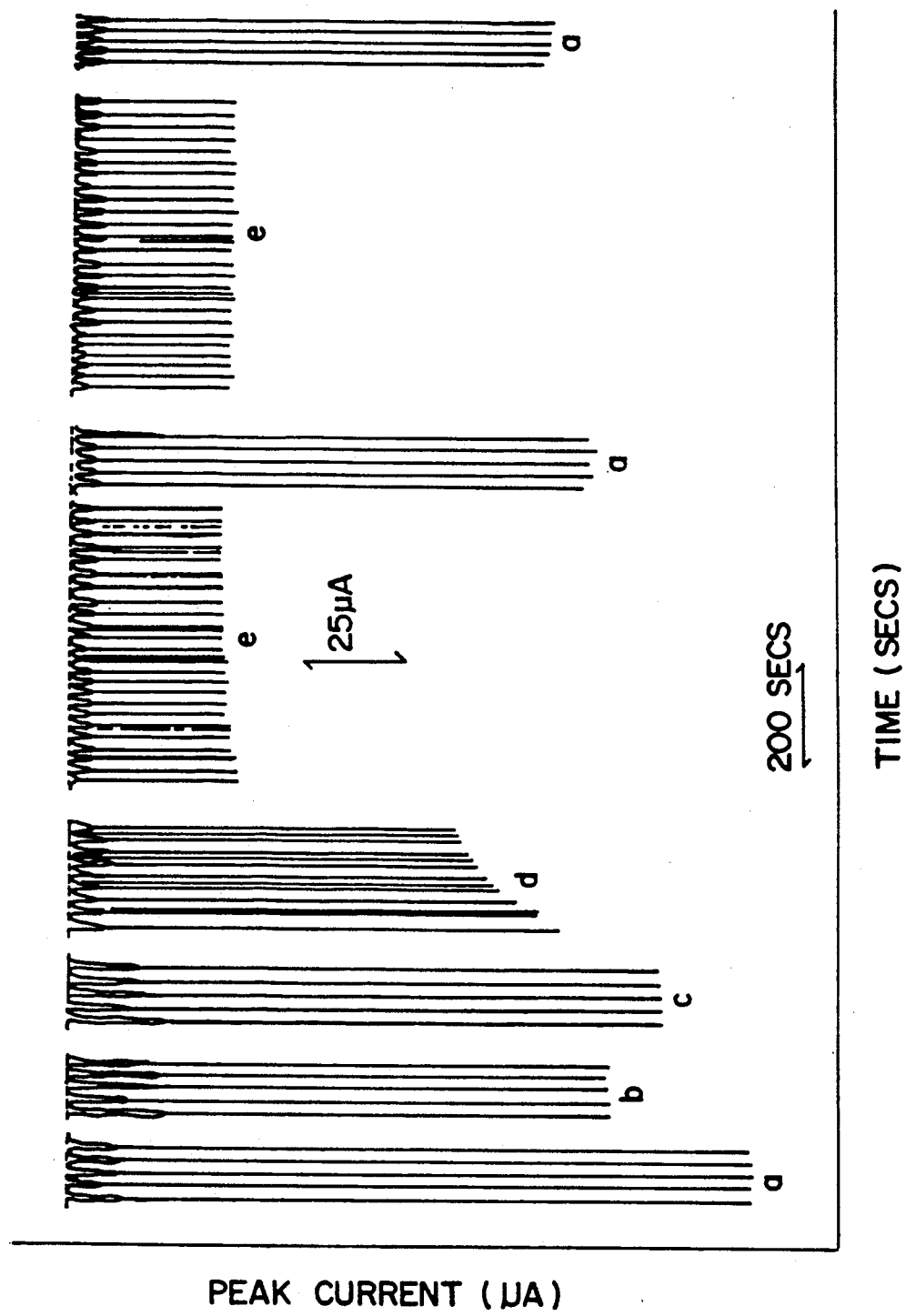
FIG. 4 is a graphical plot of the current response of an unpolymerized, platinized RVC electrode to (a) $H_2O_2$ (1 mill); (b) L-ascorbic acid (1 mill); (c) uric acid (i Mm); (d) L-cysteine (1 Mm); and (e) control human serum.

FIG. 4 shows the current response of an unpolymerized platinized RVC electrode to hydrogen peroxide (1 mM), uric acid (1 mM), L-ascorbic acid (1 Mm), L-cysteine (1 mM), and human serum. After the injection of serum, an additional sequence of hydrogen peroxide, serum, and hydrogen peroxide was injected to test for electrode fouling by proteins. The peaks obtained when human serum is injected are due to interferences, as there is no enzyme present on the electrode. Elimination of the current response due to a 1 mM concentration of interferents should assure that there will be no interferences at lower concentration levels. FIG. 4 indicates that electrode fouling due to the serum injections does occur. The hydrogen peroxide peaks decrease considerably after the first set of twenty-five serum injections (25% decrease), and then again after the second set of twenty-five injections (8% decrease). The overall decrease in the peak current after fifty injections was 31%.

Figure 5:
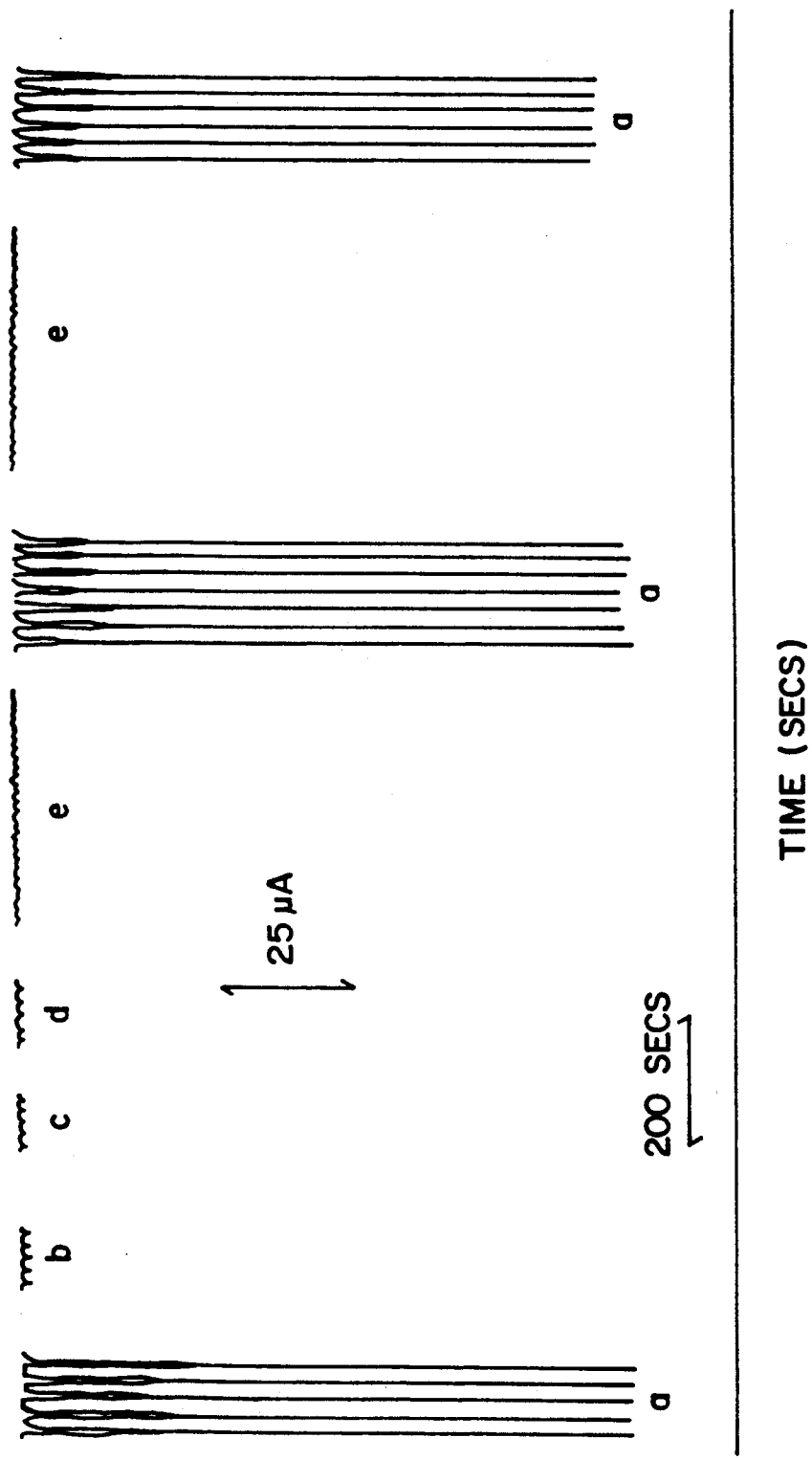
FIG. 5 is a graphical plot of the current response of a poly(1,2-diaminobenzene)-coated platinized RVC electrode to (a) $H_2O_2$ (1 MM) ; (b) L-ascorbic acid (I Mm) (c) uric acid (i mill); (d) L-cysteine (i Mm); and (e) control human serum.

FIG. 5 shows the effectiveness of the polymer film in reducing the current signal due to the interferents, while still retaining 67% of the hydrogen peroxide current signal, as compared to the unpolymerized platinized RVC. The poly(1,2-diaminobenzene) film is selective enough to allow small species, such as hydrogen peroxide, to penetrate the film, while restricting all of the interferents found in human serum.

FIG. 5 shows that electrode fouling due to protein adsorption is not problematic. Even after multiple serum injections, the hydrogen peroxide peak currents are relatively unchanged: a 5% decrease in peak current after fifty injections of serum.

Thermal Stabilization of Immobilized Glucose Oxidase by Electropolymerization with 1,2-Diaminobenzene A factor limiting the practical application of immobilized enzymes as sensing agents in known biosensors is their inactivation with elevated temperature. This thermal inactivation is believed to be a result of conformational changes in the enzyme. An improvement in the thermal stability of an immobilized enzyme is realized by means of the polymer film disclosed here. In particular, two separate methods of immobilizing glucose oxidase and the effect of an electropolymerized 1,2-diaminobenzene polymer film on the stability of the immobilized glucose oxidase are discussed below.

Glucose oxidase was immobilized to the RVC electrode surface using the carbodiimide attachment scheme of H. J. Weick, G. H. Heider, A. M. Yacynych, described in Anal. Chim. Acta, Vol. 158 (1984) pp. 137.

A glutaraldehyde attachment scheme, GOX (0.3000 g) was dissolved in 12.5% glutaraldehyde (50 mLs) which was diluted with 0.1M, pH 6.5, phosphate buffer. The plexiglass cartridges were attached to the peristaltic pump and the solution was circulated (0.8 ml/min flowrate) for three hours. The cartridges were then allowed to remain in the quiescent solution for 0.5 h. They were then rinsed with cold (4° C.) phosphate buffer (0.1M, pH 6.5) and stored overnight 4 in buffer before use.

A solution of 1,2-diaminobenzene (3 Mm) in 0.1M, pH 6.5, potassium phosphate buffer was deaerated for 0.5 h with high purity grade nitrogen prior to use, and a nitrogen atmosphere was maintained over the solution during the course of the experiment. The platinized enzyme electrode was inserted into the cell, which was connected to the peristaltic pump. The solution was circulated at a flowrate of 0.8 ml/min throughout the electropolymerization process. cyclic voltammetry was used to follow the film formation on the electrode surface. Cyclic voltammetric scans were obtained by cycling from 0.0 V to +0.8 V vs SCE, at a scan rate of 2 my/sec, until the current decreased to a minimum. Once the polymer was coated on the electrode, the cell was transferred to the FIA system where response to glucose was tested.

The cell containing the electrode was thermostatted in a water bath, of a given temperature, 0.5 h before a glucose sample was injected, to ensure thermal equilibrium throughout the entire system. The glucose standard was also immersed in the bath to prevent a temperature differential. The working buffer was also thermostatted by passing through a 50 ft (15.3 m)×1/8" (3.2 Mm) o.d. stainless steel coil placed at the bottom of the water bath; a volume of approximately 225 mls being thermostatted at all times. The potentiostat was poised at +0.38V vs RRE during all of the temperature experiments.

Figure 6:
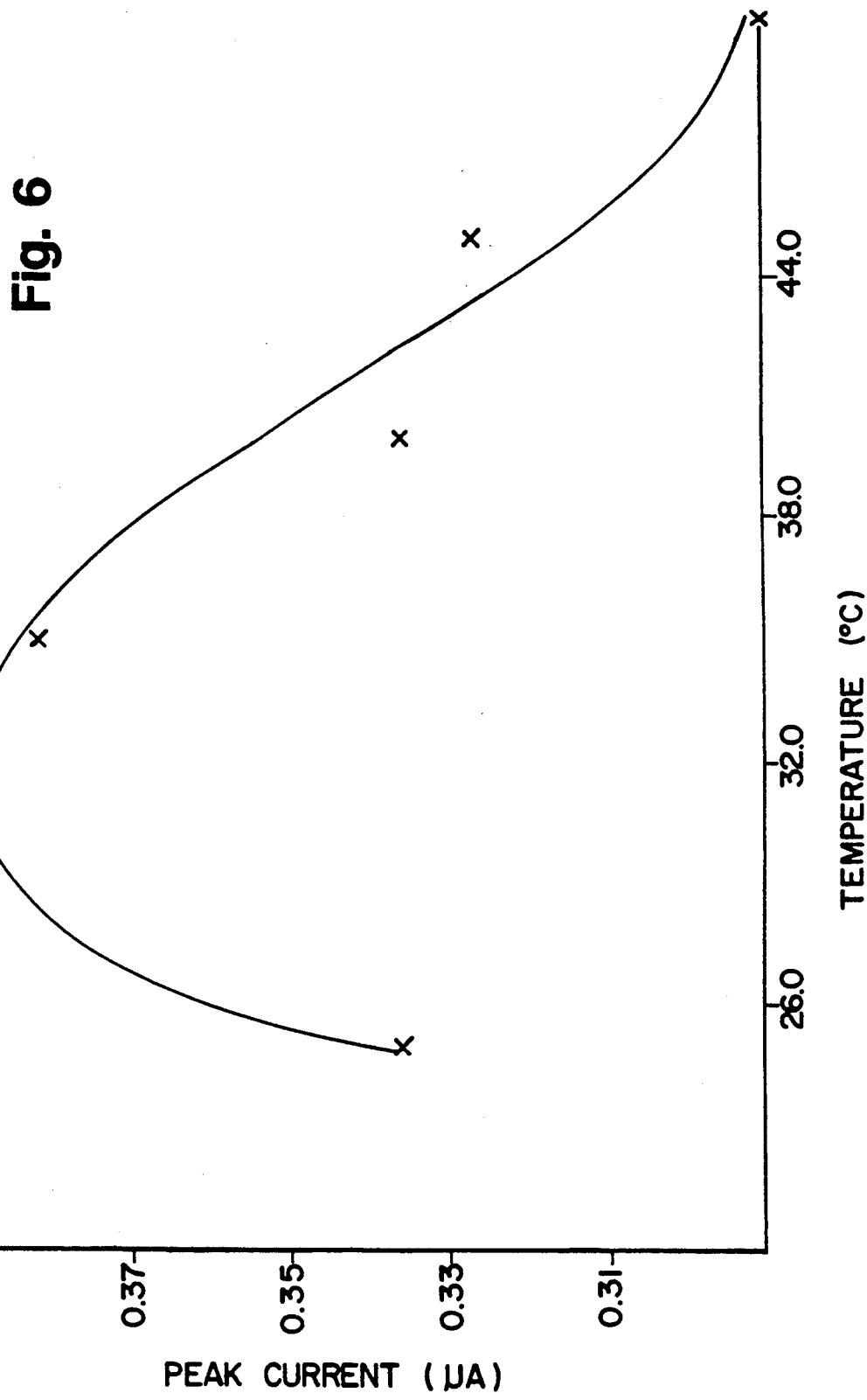
FIG. 6 is a graph of the temperature profile of a carbodiimide-immobilized glucose oxidase enzyme electrode without the 1,2-diaminobenzene polymer film for 5 μl injections of 1 mM glucose and a flowrate of 120 ml/h.
Figure 7:
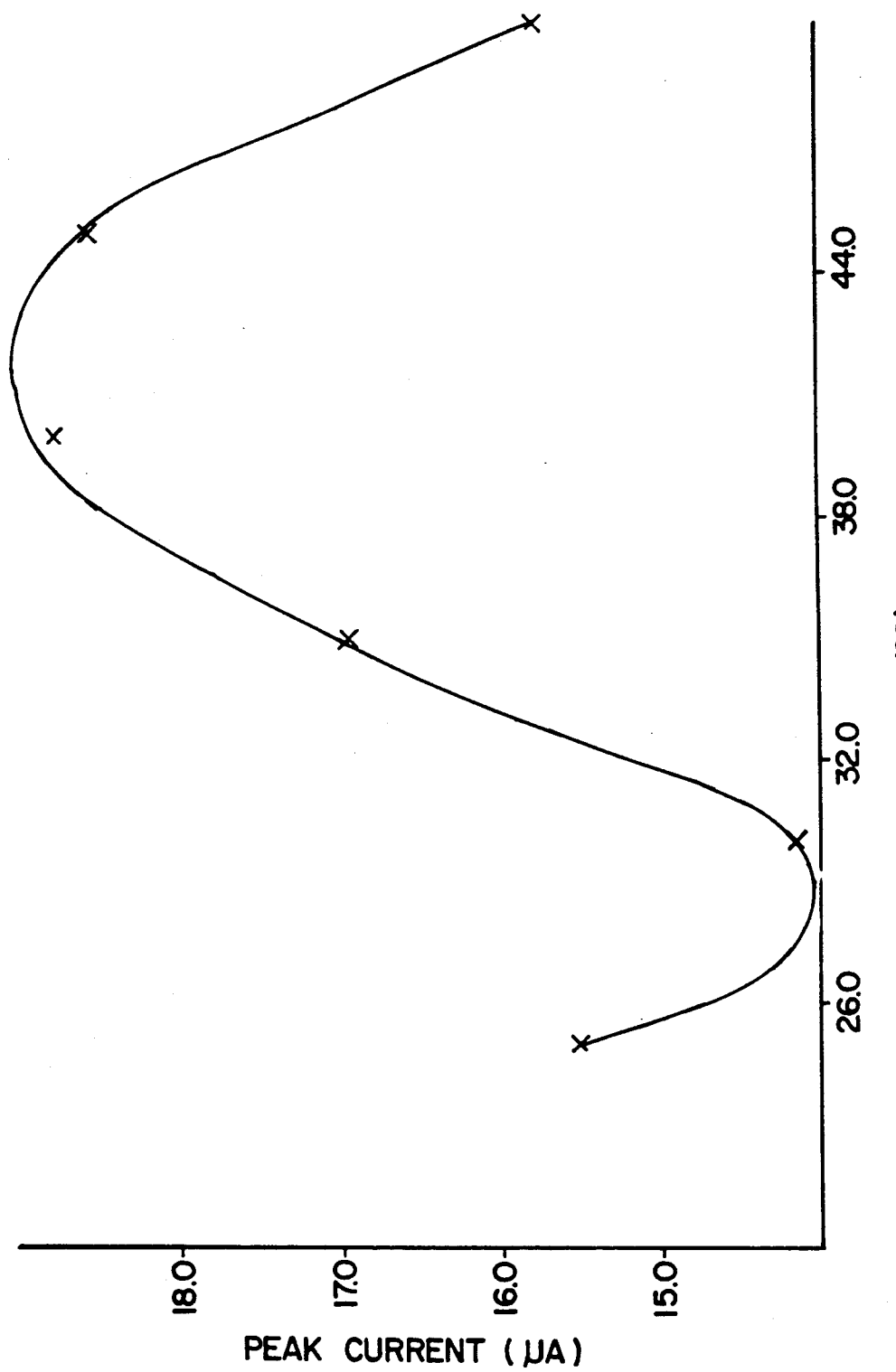
FIG. 7 is a graph of the temperature profile of a carbodiimide-immobilized glucose oxidase enzyme electrode with the 1,2-diaminobenzene polymer film for 5 μl injections of 10 mM glucose and a flowrate of 120 ml/h.

FIG. 6 shows the temperature profile of a carbodiimide-immobilized glucose oxidase electrode without the 1,2-diaminobenzene polymer film. The current responses were obtained by averaging the peak current produced by injecting five 5 μL samples of 10 Mm glucose. As can be seen from FIG. 6, the current maximum occurs at approximately 33° C. Electropolymerization of the 1,2-diaminobenzene on the surface of the glucose oxidase shifted the current maxima about 100° to 43° C., as seen in FIG. 7. Comparison of FIGS. 6 and 7 demonstrates the increase in thermal stability obtained by the polymer film.

Figure 8:
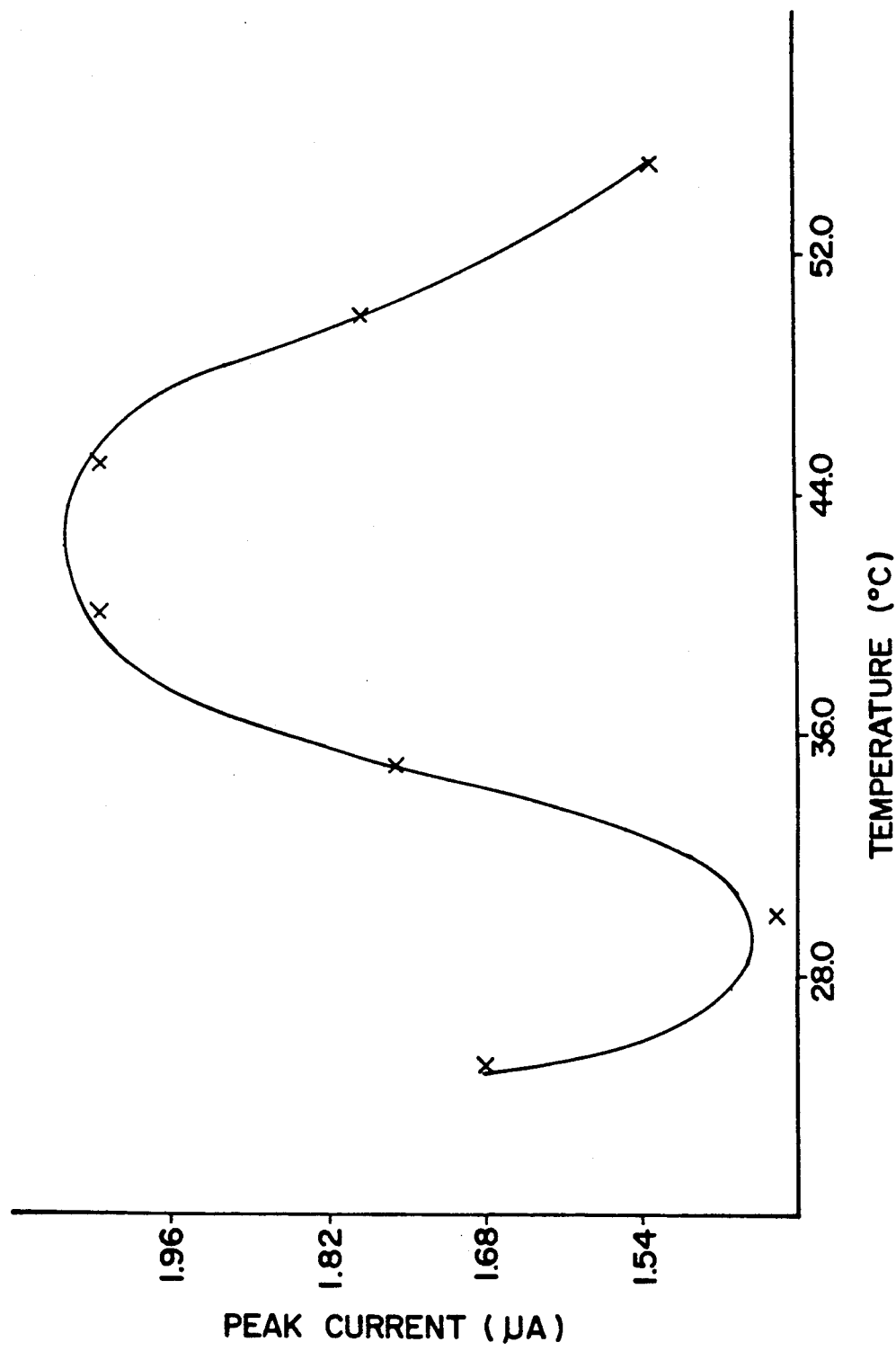
FIG. 8 is a graph of the temperature profile of a glutaraldehyde-immobilized glucose oxidase enzyme electrode without the 1,2-diaminobenzene polymer film for 5 μl injections of 10 mM glucose and a flowrate of 120 ml/h.
Figure 9:
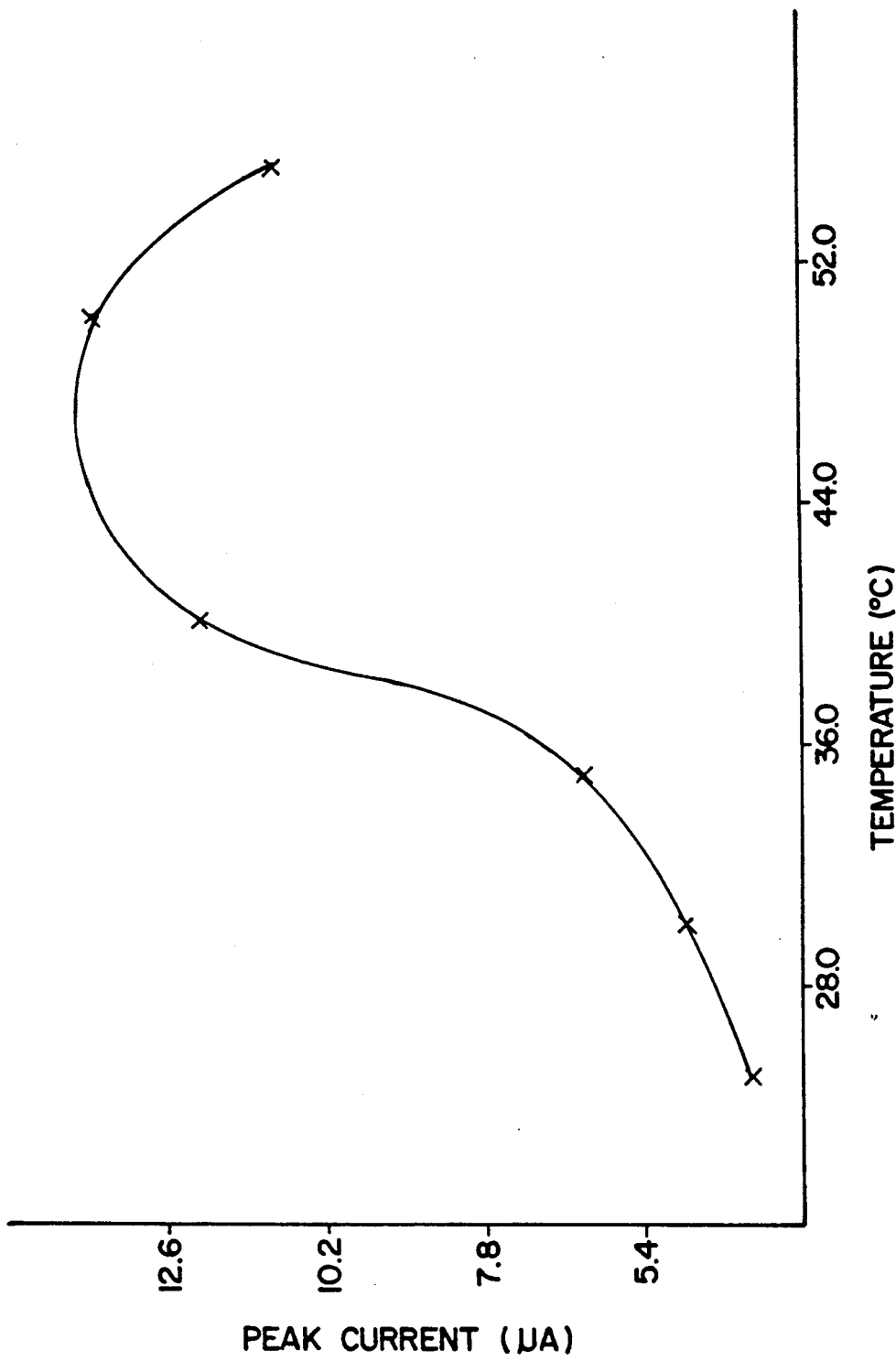
FIG. 9 is a graph of the temperature profile of a glutaraldehyde-immobilized glucose oxidase enzyme electrode with the 1,2-diaminobenzene polymer film for 5 Ml injections of 10 mM glucose and a flowrate of 120 ml/h.

The effect of the particular enzyme attachment scheme on stabilization was also studied by crosslinking the glucose oxidase to the RVC surface with glutaraldehyde, rather than bonding the glucose oxidase covalently with carbodiimide. FIG. 8 shows the effect of the immobilization technique on the thermal stabilization of the enzyme. The current maximum for the glutaraldehyde-immobilized enzyme is about 43° C., as compared to 33° C. observed for carbodiimide. Crosslinking provides increased enzyme stabilization, because the enzyme is held onto the surface of the RVC by a three-dimensional network, as compared to a single bond in the carbodiimide attachment scheme. Subsequent electropolymerization of 1,2-diaminobenzene on the surface of the glutaraldehyde-immobilized enzyme electrode results in even greater thermal stabilization, as seen in FIG. 9. In this case the current maximum was observed to be about 47° C.

Figure 10:
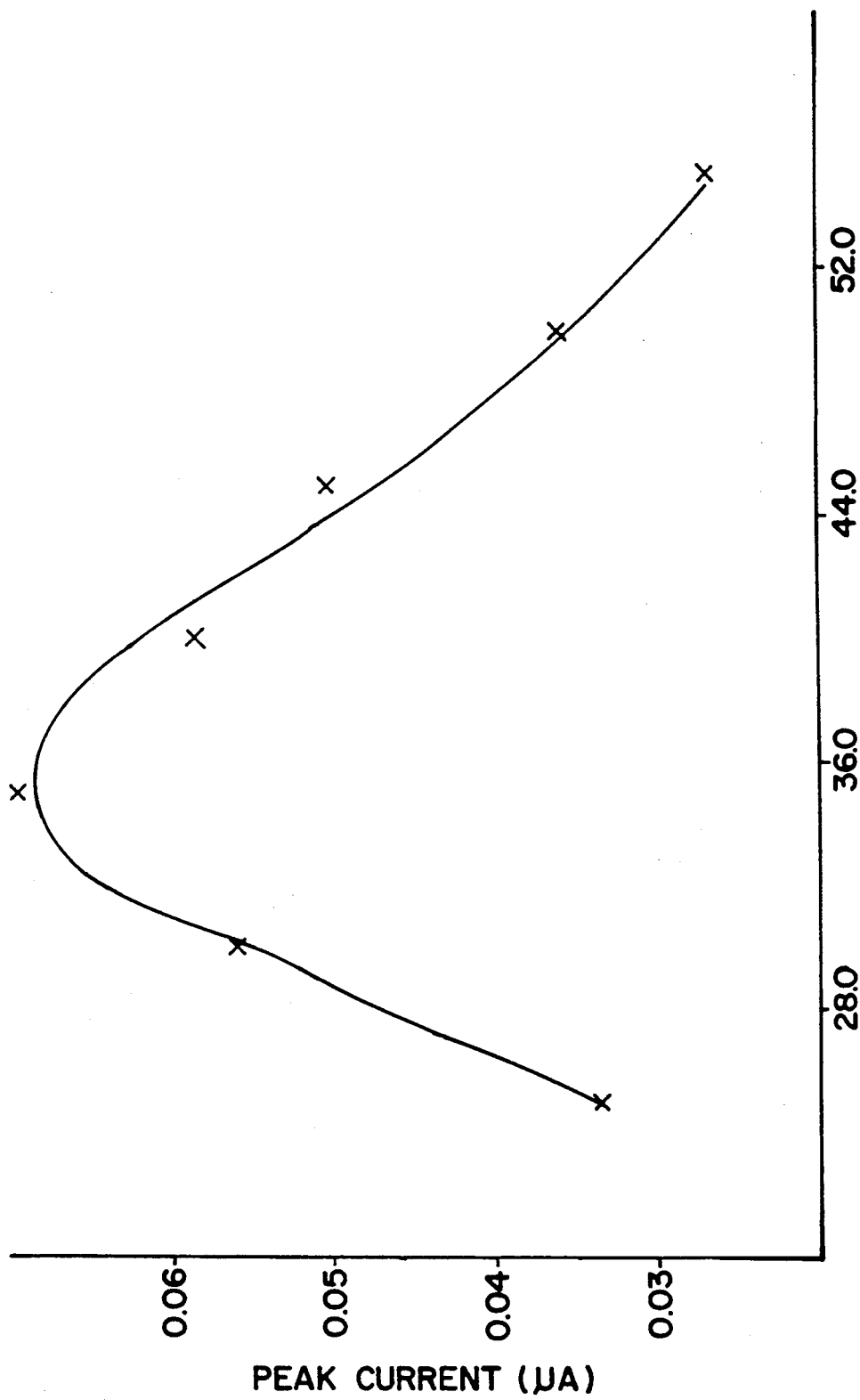
FIG. 10 is a temperature profile of free glucose oxidase.

The temperature profile of the free enzyme was also determined using FIA for comparison. A platinized RVC electrode without any polymer film or enzyme was immersed in a water bath. A mixture of glucose and working buffer was added to a test tube and allowed to equilibrate at the working temperature. After 0.5 h, glucose oxidase was added to the test tube and was timed with a stopwatch. At two minute intervals, an aliquot of the glucose-glucose oxidase mixture was injected into the FIA system. The hydrogen peroxide produced by the reaction was determined electrochemically at the electrode surface. The slope of the linear portion of the plot was used to determine the activity of the enzyme at that particular temperature. A plot of the peak current (activity) vs temperature gave a current maximum at about 35° C.; see FIG. 10.

Immobilization of glucose oxidase with carbodiamide provides little thermal stabilization compared to the free enzyme under these experimental conditions. The use of glutaraldehyde for immobilization increases the temperature maximum 8° C. over that of the free enzyme. Subsequent electropolymerization of 1,2-diaminobenzene on the immobilized enzyme increases the thermal stability by 8° C. for the carbodiimide case and 12° C. for the glutaraldehyde case, when compared to the free enzyme.

Thus, not only does the polymer film prevent fouling and prevent the interferents commonly found in human serum from reaching the electrode surface, it also increases the thermal stability of the immobilized glucose oxidase. The increased thermal stability of the enzyme directly translates into an increased operating lifetime for a biosensor constructed using electropolymerized film.

Determination of Glucose in Blood Serum by Flow Injection Analysis Using an Immobilized Enzyme Biosensor According to the Invention The performance of an illustrative biosensor according to the invention will now be described in more detail. The apparatus of FIGS. 2 and 3 was used to perform the tests described below. Unless otherwise stated, the sample volume is 5 μL and the flowrate is 120 mL/h. The output was recorded on an omnigraph model 2000X-Y recorder available from Houston Instruments of Austin, TX. Either a Varian model 8500 syringe pump, available from Varian Instruments of Palo Alto, Calif. or the DuPont model 870 HPLC Pump referred to above was used for the FIA work. Samples were introduced into the carrier stream with a Rheodyne model 7125 injection valve available from Ace Chemical Co. of East Brunswick, N.J., having a 5 μL sample loop. The electrodes constructed have a cell void volume of approximately 130 μL and dilution of the sample is dependent on the sample volume size.

Electrochemical deposition of platinum was performed using an ECO Model 549 potentiostat/galvanostat available from ECO Instruments Inc. of Cambridge, Mass. The Rabbit peristaltic pump referred to above was used to circulate the solutions through the RVC electrodes for the platinum plating, the enzyme attachment procedure, the activity assay of the immobilized enzyme electrodes, and electropolymerization of the polymer film.

The enzymatic assays were performed using a Perkin-Elmer model 101 spectrophotometer available from Perkin-Elmer Corp. of Norwalk, Conn., equipped with a flow cell (1 cm path length). The absorbance was recorded on a Recordall strip-chart recorder available from Fisher Scientific Supply, of Springfield, N.J. A Bausch and Lomb Spectronic 20 UV-Vis spectrophotometer, available from Fisher Scientific Supply of Springfield, N.J., was used to determine the protein loading on the electrodes.

Controlled Human Serum (SRM-909) and Diluent (National Institute of Standards and Technology, Washington, DC) was prepared according to NBS specifications. Control Serum, Type I-A: Normal; Assayed, available from Sigma Chemical Co. of St. Louis, Mo., was used to test the stability of the 1,2-diaminobenzene polymer film. The serum was reconstituted with 0.1M, pH 6.5 phosphate buffer.

The Coomassie Brilliant Blue G-250, available from Fisher Scientific Supply Co. of Springfield, N.J., for the protein loading assay was used as received. All other chemicals were of reagent grade, and distilled-deionized water was used for all tests. The $N_2$ used during the electropolymerization of 1,2-diaminobenzene was of high purity, available from Jersey Welding of Piscataway, N.J.

Glucose oxidase (IIGOXII) was then immobilized on a platinized RVC electrode via the glutaraldehyde crosslinking attachment scheme described above. The electrodes immobilized with glutaraldehyde had an enzymatic activity of almost 1.5 times that of the carbodiimide-immobilized electrodes; 0.1254±0.0108 vs. 0.0936±0.0152 μM units per electrode. The use of the glutaraldehyde attachment scheme also does not require carbonaceous sites on the RVC; hence, a completely platinized RVC electrode, a platinum wire, or any other type of conducting material may be used as the base electrode.

Once immobilized with GOX, the electrodes were electropolymerized with 1,2-diaminobenzene ("DAB"). The activity of the immobilized enzyme was determined both before and after the electropolymerization of the DAB. After completion of the enzymatic assay, the electrodes were evaluated in the FIA system at a working potential of +0.6 V vs SCE or +0.38 V vs RRE. A correlation study between enzyme activity and current response was also performed.

Protein Loading Assays

Protein loading assays were performed according to a modified procedure described by M. M. Bradford in Anal. Biochem., Vol. 72 (1976), U, pp. 248–254. Coomassie Brilliant Blue G-250 (100 mg) was dissolved in 95% ethanol (50 mL). To this solution 854 (w/v) phosphoric acid was added (100 mi). The resulting solution was diluted to 1 liter. Final concentrations in the protein reagent were 0.01% (w/v) Coomassie Brilliant Blue G-250, 4.7% (w/v) ethanol and 8.5% (w/v) phosphoric acid. The glucose oxidase stock solution consisted of 0.1 g/mL GOX in 12.5% glutaraldehyde which was diluted in 0.1M, pH 6.5 phosphate buffer.

A calibration curve for glucose oxidase was prepared as follows for use in protein loading assays. Protein solutions containing 100-900 #g GOX in a volume up to 0.1 mL were piped into Bausch and Lomb Spectronic 20 Colorimeter test tubes. The volume in the test tube was adjusted to 0.1 mL with 12.5% glutaraldehyde solution in 0.1M, pH 6.5 phosphate buffer. Five milliliters of the protein reagent was added to the test tube, and the contents mixed by inversion. The absorbance at 595nm was measured after 2 minutes but before 1 hour against a reagent blank prepared from 0.1 mL of the 12.5% glutaraldehyde in phosphate buffer and 5 mL of the protein reagent. The weight of the glucose oxidase was plotted versus the absorbance, and the resulting curve was used to determine the protein loading in the unknown sample.

The total protein loading on the electrode surface was determined using a difference method. Specifically, the total GOX in the immobilizing solution was calculated both before and after immobilization of the enzyme and the difference in the absorbance reading was used to determine the amount of protein on the electrode surface.

The total amount of protein immobilized on the electrode surface for four different enzyme electrodes is shown in Table I. The corresponding enzymatic activity of each electrode is also shown.

TABLE I

| GOX SENSOR PROTEIN LOADING AND ENZYMATIC ACTIVITY ASSAY | | |
|---|---|---|
| Sensor Under Test | Protein Loading ($\mu$g/electrode) | Enzymatic Activity ($\mu$M Units/electrode) |
| 1 | 38 | 1.1318 |
| 2 | 31 | 0.1315 |
| 3 | 72 | 0.1130 |
| 4 | 37 | 0.0921 |

The correlation between the two factors is affected by the amount of immobilized protein which is activated. There is sufficient enzyme, however, to give a current signal well above the noise level. An electrode which exhibits an activity of 0.01 $\mu$M units/electrode or greater will generally produce a large enough current response to be useful.

Lifetime Studies

Both the working lifetime and the shelf lifetime of the electrodes were determined by injecting a 5 $\mu$L portion of a 10 mM glucose standard into the FIA system and measuring the resulting current. When not in use, the enzyme electrodes were stored in 0.1M, pH 6.5 phosphate buffer at 4° C. The electrodes used for the working lifetime study were used daily for at least 3 hours. Those tested for shelf lifetime were used only for the test, which was only once or twice a week for a few minutes.

The average working lifetime was determined to be 1.5 to 2 months, while the shelf lifetime is over 3 months. The lifetime was determined by injecting 5 $\mu$L of a 10 Mm glucose standard into the FIA system. The electrode is still useful even if the current response for 10 Mm glucose falls below 1 $\mu$A. The ultimate factor affecting its usefulness is the signal-to-noise ratio. The sensor's response is almost instantaneous at a flowrate of 2 mL/min, yielding a sampling rate of about 130 samples per hour.

Kinetic Studies

Along with protein loading and enzymatic activity assays, kinetic data were also obtained to characterize the enzyme electrodes.

The kinetic data on immobilized GOX were obtained by continuous flow analysis. The electrode was inserted into the flow cell, which was connected to the peristaltic pump. A potential of +0.6 V vs SCE was applied, and the electrode was allowed to reach equilibrium (about 15 minutes) as a buffer solution of 0.1M, pH 6.5 potassium phosphate circulated through the system at 2 ml/min. Once equilibrium was reached, a steady baseline for the buffer solution was recorded, and a known concentration of glucose in the working buffer was then circulated through the cell until a current plateau was reached. This procedure was repeated for a variety of standard concentrations. The current produced by the enzymatic reaction was measured and plotted against concentration.

The apparent $K_m$, $K_m'$, of the immobilized enzyme were determined amperometrically using a "Lineweaver-Burk" type equation as discussed by Kamin and Wilson in *Anal. Chem.*, Vol. 72 (1980), pp. 248-254. For an unpolymerized immobilized enzyme the reaction rate and the current measured for enzymatic product detection under conditions of substrate saturation (for a given substrate concentration) had values of 5.01 mM and 189.06 $\mu$A, respectively. The same test was also performed after the enzyme electrode was electropolymerized with 1,2-diaminobenzene. In this case, the corresponding values were found to be 25.04 mm and 46.60 $\mu$A, respectively.

Enzymatic Activity vs Current Response

Figure 11:
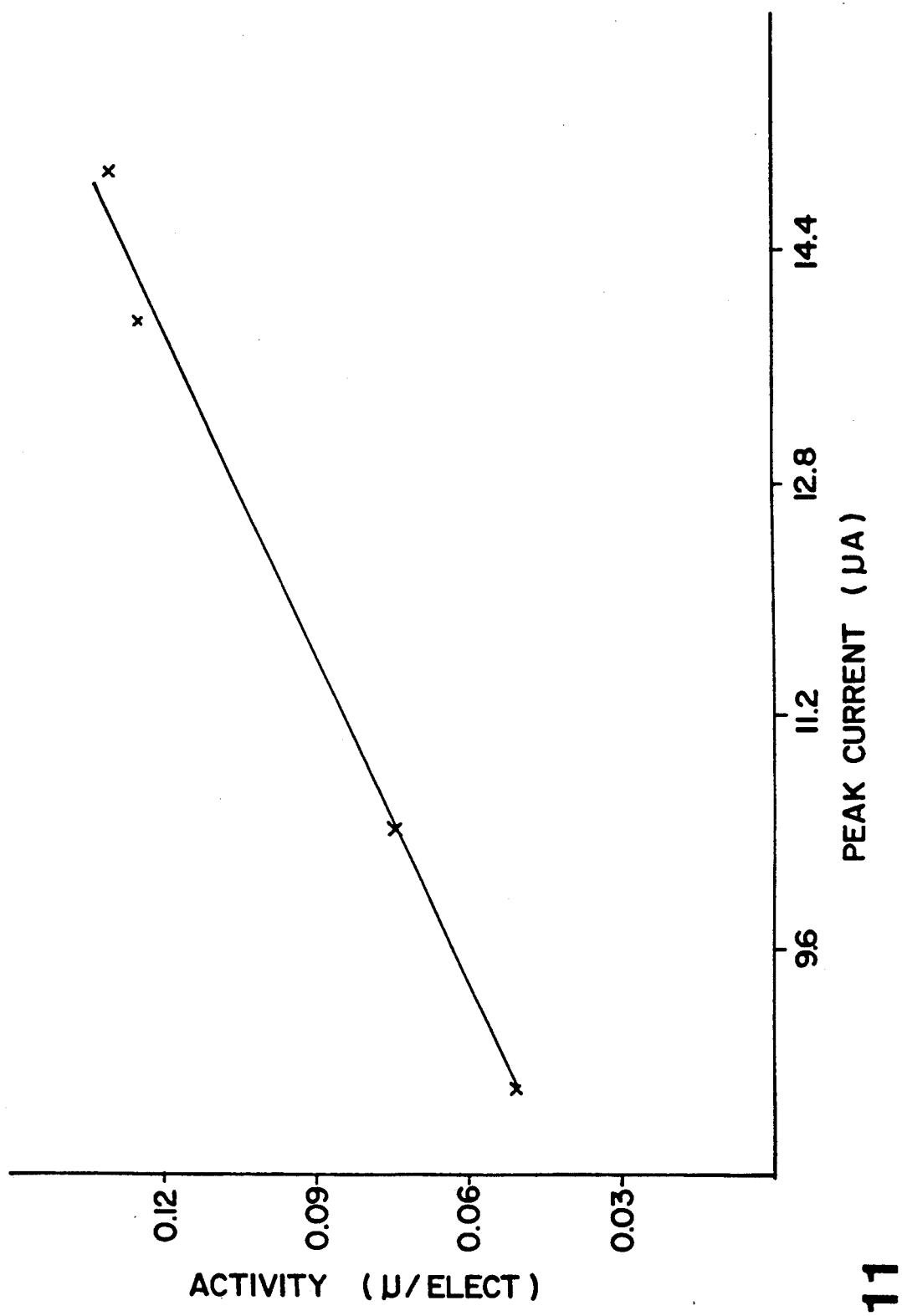
FIG. 11 is a graph showing the correlation between enzymatic activity (μM units/electrode) and peak current (μA) for a glucose oxidase electrode. For the peak currents, 5 μL of a 10 mM glucose standard was injected. The flow rate was 120 mL/h.

FIG. 11 shows a representative correlation between the activity of the glucose oxidase on the electrode surface and its corresponding current signal obtained with the FIA system. The slope and correlation coefficient of the data are 0.0134 $\mu$M units/electrode/$\mu$A and 0.997, respectively. The complex nature of the platinized RVC surface plays a key role in the amount of current obtained. As the same intricate surface is not generally reproducible, a correlation is observed only for individual electrodes.

Electrode Response to Serum

As an absolute check on the validity of the glucose sensor, the glucose level in a sample of human serum (obtained from the National Institute of Standards and Technology) was determined using four different electrodes. The values obtained are listed in Table II.

TABLE II

| SERUM GLUCOSE DETERMINATIONS | |
|---|---|
| *SRM-909 Value | 6.41 ± 0.39 mM |
| Glucose Sensors | 1. 6.35 ± 0.14 mM |
|  | 2. 6.56 ± 0.22 mM |
|  | 3. 6.66 ± 0.14 mM |
|  | 4. 6.27 ± 0.18 mM |
| Average Value | 6.46 ± 0.18 mM |

*NIST Standard Reference Material

The range of glucose concentrations reported by the sensors of the present invention tightly overlaps the NIST value. The average concentration of all four sensors is 6.46±0.18 mM, giving an error in accuracy of less than one percent.

This glucose biosensor has the advantage of a long lifetime (1.5–3 months), a large working range and linear range (0–100 mM and 0–30 mM, respectively), and a high sample throughput (130 samples/hour). It is also quite reproducible with a precision of less than ±1%, as well as excellent accuracy as determined by the NIST standards. This type of biosensor could also be miniaturized, as the various components are constructed chemically, and any size or shape of base electrode could be used. The sensor may also be useful in the determination of glucose in other fluids such as urine, carbonated drinks, alcoholic drinks, juices and many other samples containing glucose.

Additional examples of the preparation of the surface-modified electrochemical biosensors of the present invention are as follows.

Biosensor without Electron Mediator

Apparatus

A variety of electrodes made from different materials and surface geometries were used for biosensor construction, including, but not limited to, the following conducting materials: reticulated vitreous carbon (RVC), glassy carbon, carbon fibers, pyrolytic graphite, microarray and microhole array carbon electrodes, gold, and platinum.

Materials 1,2-diaminobenzene (DAB), 90% (Aldrich, Milwaukee, Wisc.) was recrystallized three times with dichloromethane; 1,3-DAB, 99+% (Aldrich) and 1,4-DAB, 99.5% (Pfaltz-Bauer, Waterbury, Conn.) were used as received. Catechol (99+%), resorcinol (98%), and hydroquinone (994) were recrystallized by ordinary techniques or by sublimation.

Phosphate buffer (0.1 M, pH 6.5) was prepared with distilled-deionized water using ACS certified (Fisher, Springfield, N.J.) phosphate salts. The pH was adjusted to 6.5 or 7.4 (sect. 2,3,2,3 and 2,3,2,7) with concentrated phosphoric acid or potassium hydroxide. Sodium azide (Aldrich) was added (0.1% wt/wt) to the buffer solution to prevent bacterial growth. Hydrogen hexachloroplatinate (IV) hydrate (ACS reagent, Aldrich) was used for platinization. other chemicals used were L-ascorbic acid (Fisher, certified ACS); 4-acetamidophenol, 98% (Aldrich); uric acid, 99+% (Aldrich); and B-D(+)-glucose (Sigma, St. Louis, MO). Hydrogen peroxide solutions were prepared in phosphate buffer by making appropriate dilutions of a 3% solution (York Pharmacal, Brookfield, Mo.) or of a 30% solution (J. T. Baker, Phillipsburg, N.J.). Glucose oxidase (Sigma, Type II from *Aspergillus niger*); glutaraldehyde, 25% (wt%) (Aldrich). Reticulated vitreous carbon (RVC - 80S) was obtained from The Electrosynthesis Co., Inc., East Amherst, N.Y.

Procedure

A constant potential of a +0.60 V vs SCE was used for most studies, except glassy carbon electrodes (GC) (+0.80 V vs Ag/AgCl) and platinum (Pt) and partially platinized glassy carbon electrodes (Pt/GC)(+0.60 V vs Ag/AgCl).

Electrochemical deposition of platinum onto RVC electrodes was done by circulating a solution of 0.025 M hexachloroplatinate in phosphate buffer through the electrode at 5 ml/min for 6 h, while operating the potentiostat/galvanostat in the galvanostatic mode at a current density of $-0.39$ ma/cm$^2$. For the platinization of glassy carbon, thin-layer electrodes, the solution was circulated at 5 mL/min for 1 h, while operating galvanostatically with a current density of $-3.9$ mA/cm$^2$ or $-1.95$ mA/cm$^2$. The platinized electrodes were characterized by measuring response to 1 mM $H_2O_2$, 1 mM acetaminophen, 1 mM ascorbic acid, and 1 mM uric acid.

Glucose oxidase (GOX) was immobilized by cross-linking with glutaraldehyde by dissolving 0.3 g of GOX in 50 mL 12.5 wt % glutaraldehyde (25 mL, 25 wt % glutaraldehyde and 25 mL, 0.1 M, pH 6.5 phosphate buffer). The enzyme solution was circulated through the electrodes at 0.8 ml/min for 3 h with a peristaltic pump. The electrodes were left in the quiescent solution for 0.5 h, then rinsed with cold (4° C.) phosphate buffer, and stored at 4° C. in buffer overnight before testing their response to glucose.

Diaminobenzene and dihydroxybenzene isomers were electropolymerized using a 3 mM solution of the isomer(s)) in potassium phosphate buffer (0.1 M, pH 6.5), which was deaerated for 0.5 h with high purity nitrogen, and was circulated at 0.8 ml/min with a peristaltic pump. For films containing two monomers, the total solution concentration was 3 mM (e.g., 1.5 mM of each monomer). The potential was continuously cycled from 0.00 V to 0.80 V vs SCE at 2 mv/sec until the current decreased to a minimum, which indicated complete coverage of the surface with the polymer. For RVC electrodes this took 18–24 h, depending on the film. The electropolymerization of 1,3-DAB/resorcinol on Pt electrodes was done for various times (from 1 to 21 h), because initial results with only 4 scans (<1 h) were unsatisfactory. For the partially platinized glassy carbon electrodes, electropolymerization times of 2 and 3.33 h were used.

A number of glucose biosensor electrodes were prepared using different monomer compositions to prepare the electropolymerized film covering the sensing surface. They were then compared in terms of their ability to ignore the presence of acetaminophen in a biological sample. The results for the sensors prepared using reticulated vitreous carbon electrodes are reported in Table III. As shown there, the most effective monomer composition was an equimolar mixture of 1,3-diaminobenzene and resorcinol. Reported in the table are the long-term slopes of response to 1 mM acetaminophen. The lower the slope number, the better the ability of the polymer film to prevent interference from acetaminophen. Monomer ratios (which are all 1/1) are on a molar basis. For each type of sensor a number (at least three) were prepared by the exact same procedure and tested. Thus the table reports for each type of sensor a range of values, from the lowest slope observed to the highest, and a range of days studied, from the electrode studied for the shortest period of time to the electrode studied for the longest period.

TABLE III

| Sensor Type No. | Monomer Composition | Range of Values for Slope of Response to Acetaminophen (× 100) | Days Studied |
|---|---|---|---|
| 1 | 1,2-DAB | 2.6–25 | 80–110 |
| 2 | 1,3-DAB | 0.5–2 | 64–118 |
| 3 | 1,4-DAB | 0.6–4.3 | 76–114 |
| 4 | 1,2-DAB/ 1,3-DAB (1/1) | 1.2–15.0 | 64–123 |

TABLE III-continued

| Sensor Type No. | Monomer Composition | Range of Values for Slope of Response to Acetaminophen (× 100) | Days Studied |
|---|---|---|---|
| 5 | 1,2-DAB/Catechol (1/1) | 8-50 | 40-166 |
| 6 | Catechol | 0.7-1.5 | 111-115 |
| 7 | Resorcinol | 8.5-9.0 | 80-82 |
| 8 | 1,3 DAB/Resorcinol (1/1) | 0.003-0.76 | 131-280 |
| 9 | Hydroquinone | Did not sufficiently polymerize on the electrode surface. | |

The best ratio of 1,3-DAB/resorcinol for the electropolymerized film, to block interferents, was determined by using three electrodes (without enzyme) at each of nine different DAB/resorcinol molar ratios: 100/0, 87.5/12.5, 75/25, 62.5/37.5, 50/50, 37.5/62.5, 25/75, 12.5/87.5, and 0/100. The best ratio was found to be in the range of about 50/50 to 62.5/37.5 (1,3-DAB/resorcinol). The polymerization proceeds by dehydrogenation of the amine and hydroxyl groups and covalent bonding of the nitrogen and oxygen atoms to ring carbons of the adjacent monomer molecules.

Biosensor with Electron Mediator

All current electrochemical sensors for glucose have drawbacks. The more serious problems include dependence of the sensor on oxygen, adsorption of biomacromolecules (fouling) such as proteins to the electrode surface that hinder the performance of the sensor, interfering electrical signals from other molecules that lead to erroneous readings, and for sensors where an electron mediator is used in place of oxygen, the working lifetime of the sensor is compromised by the stability of the mediator.

To address those drawbacks one can modify a graphite electrode in three simple steps, yielding a working glucose biosensor. The entire modification takes less than two hours and the working sensor lasts at least one month without any further modification. The sensor, which uses a ferrocene compound as an electron mediator in place of oxygen, successfully solves the major problems outlined above. Through the use of a very thin (approximately 10 nm) electropolymerized film, both electrode fouling and interferences are prevented, there is little or no dependence on oxygen due to the presence of the mediator, and the film prevents the mediator from leaching from the sensor surface. These sensors are the first electrochemical glucose biosensors which prevent fouling and interference, are not dependent on oxygen, and have good stability and lifetime.

Electron mediators (e.g., ferrocenes) take the place of oxygen to recycle the inactive form (i.e., reduced) of the oxidoreductase enzyme to the active form (i.e., oxidized). This is shown schematically in FIG. 22, where glucose oxidase (GOX) is used as an example, although this approach is applicable for most oxidoreductase enzymes.

Figure 22:
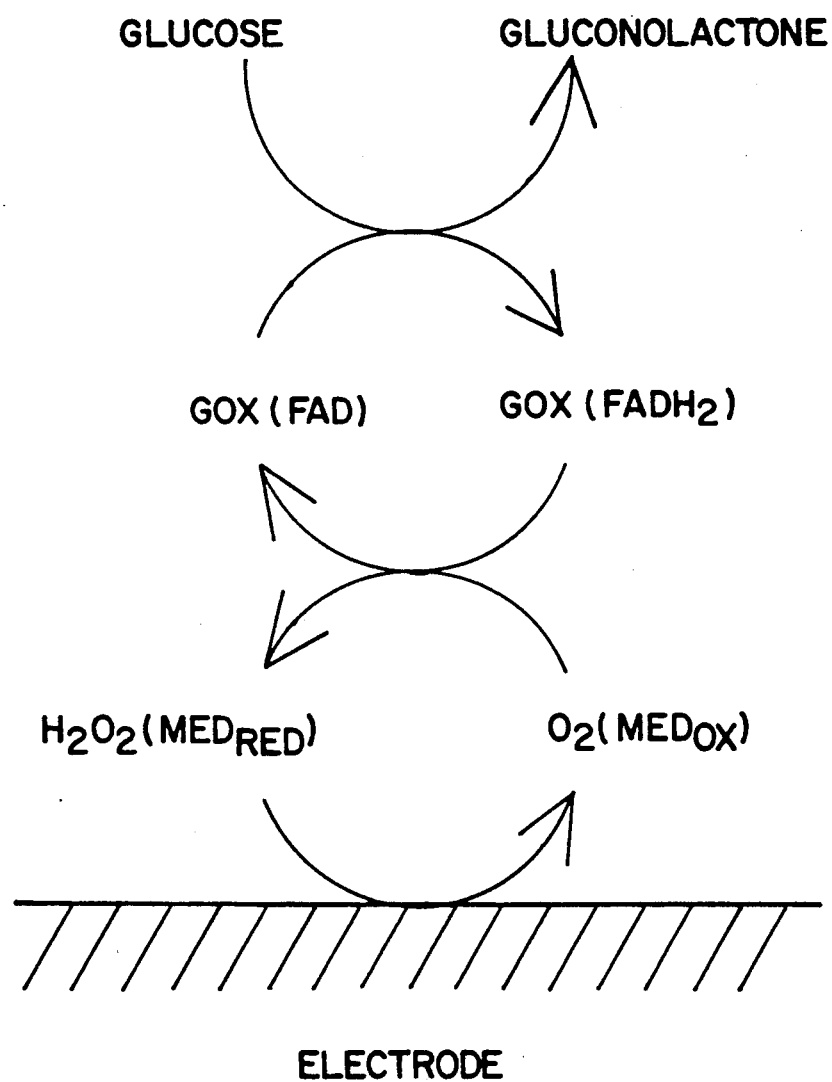
FIG. 22 is a schematic representation of the reaction cycles that take place at and above the electrode surface of a glucose biosensor, using either oxygen or an electron mediator.

Oxygen becomes the limiting factor in the enzymatic reaction at high substrate concentrations, due to its limited solubility in aqueous solutions. To solve this problem, electron mediators can be used to recycle the enzyme. They are called electron mediators because they mediate the electron transfer to regenerate the enzyme by oxidizing the prosthetic group at the active site, and then the mediator is oxidized at the electrode, as shown in FIG. 22.

Desirable factors for electron mediators include: 1) Confining the mediator to the enzyme layer (although this is not a requirement). 2) Completely reversible redox behavior and a moderate oxidation potential. Ideally, the redox potential would be as low as possible, but it does need to be more positive than the redox potential of the enzyme. For free glucose oxidase (i.e. not crosslinked or adsorbed), $E° = -0.063$ V ($-0.285$ V vs SCE). Interference from reduction of oxygen is a problem at moderately negative working potentials. Therefore, most work involving mediators aims to use a working potential close to 0.00 V vs SCE or slightly more positive. With higher oxidation potentials, the sensor requires a longer time to reach a stable baseline; background current and noise will be higher; and the number of interferents electrolyzed will increase. 3) The mediator should be stable in both its oxidized and reduced forms. 4) The electron transfer rates between the mediator, and both the enzyme and the electrode, should be as fast as possible. 5) It should not react with oxygen or any other species present in the test solution.

The advantages of electron mediators are: less dependence on low ambient oxygen concentration, which extends the linear response at high substrate concentrations and also circumvents the problem of the variation in ambient oxygen concentration; a lower working potential is possible because hydrogen peroxide is not sensed; at a lower working potential there is less interference from electroactive species; and the enzyme is not deactivated by hydrogen peroxide, which is no longer produced. (Hydrogen peroxide is no longer produced in deoxygenated solutions. In ambient solutions, production of hydrogen peroxide from reduction of oxygen competes with mediator reduction; therefore, less hydrogen peroxide is produced.)

The mediated biosensors overcome many of the problems associated with oxygen-based biosensors. This is done by an all-chemical means of construction by electropolymerization of a non-conducting film, adsorption of a ferrocene derivative, and immobilization of glucose oxidase onto carbon or platinized carbon electrodes. There is little to no dependence on oxygen resulting in expanded linear range, and a much lower working potential on carbon is realized ($+0.15$ vs 0.90 V vs SCE). Vastly improved linearity well beyond the clinical or diabetic range is obtained (up to 95 mM). Electroactive interferents are screened out and fouling of the electrode is prevented. In addition, the film retains the mediator in the sensing layer, providing previously unachieved lifetime and stability.

Figure 23:
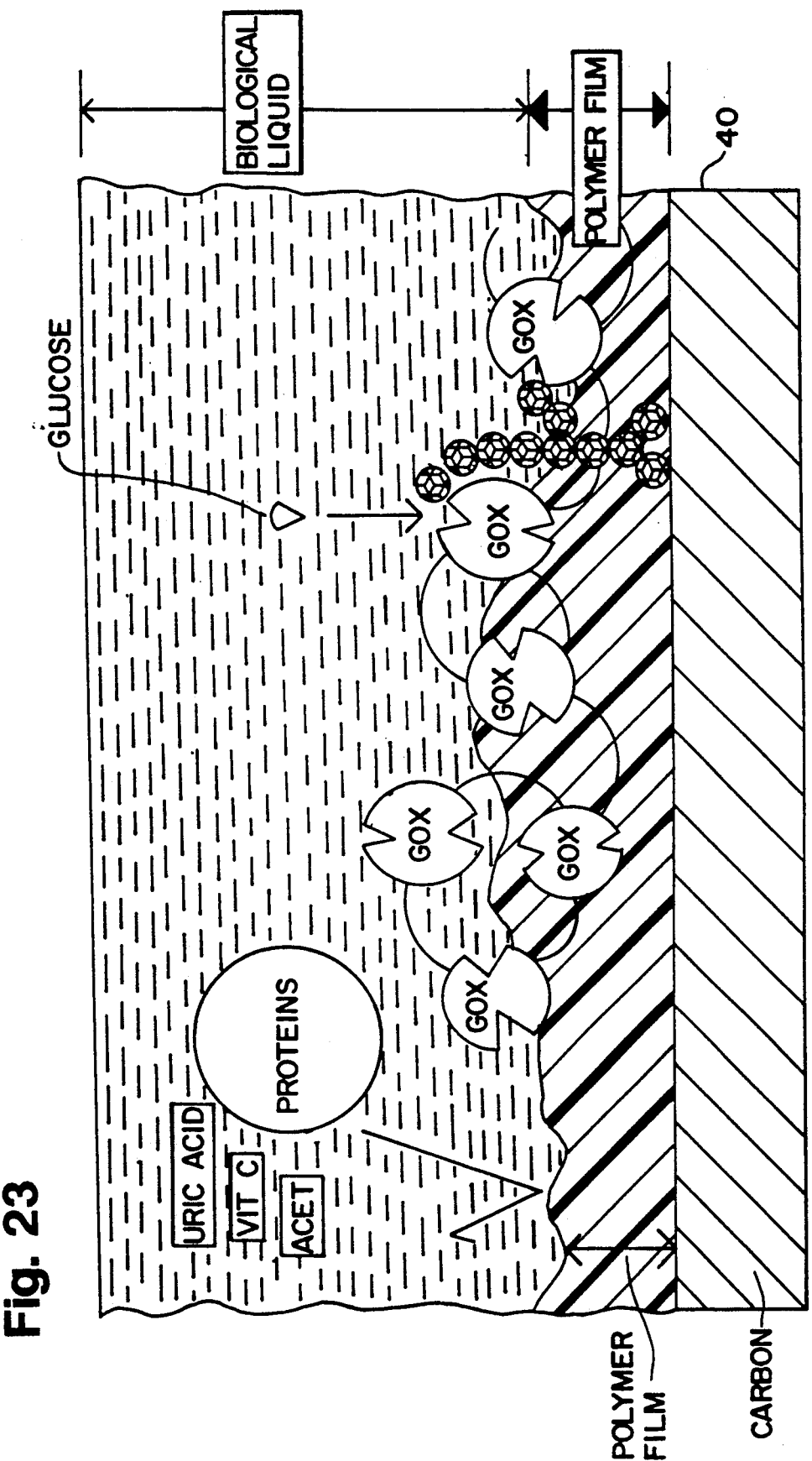
FIG. 23 is a schematic representation, similar to FIGS. 1a and 1b, of a portion of the contact surface of a glucose biosensor of the present invention, in which an electron mediator is included in the polymer layer.

Without being bound by theory, we believe the sensors works as constructed because the addition of the solution of mediator causes the polymeric film to swell, allowing the mediator to penetrate the film. As the solvent evaporates, the film shrinks around the ferrocene, thus holding the mediator in place. Now there is a network of ferrocene molecules throughout the film, from the biological liquid interface to the electrode surface. Thus, the GOX immobilized at the surface of the film is electrically connected to the electrode surface through this network of ferrocene molecules. We believe that charge is transferred from ferrocene molecule to ferrocene molecule. This is depicted schematically in FIG. 23. The ferrocene derivative electron mediator is represented by the circles with hexagons.

This drawing demonstrates how the mediator is in contact with the active site of the enzyme as well as the electrode surface through a network of ferrocene molecules.

Apparatus

An ECO Instruments (Newton, Mass.) Model 549 potentiostat/galvanostat was used for platinization. All other experiments were done using either an EG&G Princeton Applied Research (Princeton, N.J.) Model 264A potentiostat or an EG&G PAR Model 174 potentiostat.

Materials

3-Aminophenol, 98% (Aldrich) was used as received. 1,3-DAB, 99+% (Aldrich) was recrystallized by ordinary techniques or by sublimation.

Phosphate buffer (0.1 M, pH 7.4) was prepared with distilled-deionized water using ACS certified (Fisher, Springfield, N.J.) phosphate salts. The pH was adjusted to 7.4 with concentrated phosphoric acid or potassium hydroxide. Other chemicals used were Alphahydroxyethylferrocene (Pfaltz & Bauer, Waterbury, Conn., 1,1'-dimethylferrocene (Lancaster Synthesis, Windham, N.H.), L-ascorbic acid, 99% (Aldrich), 4-acetamidophenol, 98% (Aldrich), and B-D(+)-glucose (Sigma, St. Louis, Mo.). Hydrogen peroxide solutions were prepared in phosphate buffer by making appropriate dilutions of a 30% solution (J. T. Baker, Phillipsburg, N.J.). Platinum salts: hydrogen hexachlorplatinate (IV) hydrate (Aldrich).

Glucose oxidase was from Sigma (Type II from *Aspergillus niger*) and glutaraldehyde, 25% (wt %) was from Aldrich.

Procedure

First the electrodes were constructed by sealing spectroscopic grade graphite rods in glass tubing with epoxy resin. Copper wire was epoxied to the graphite extending outside the glass tube to provide the electrical connection. The electrodes were then filed down and polished by normal methods, resulting in flush disk electrodes.

Then partial platinization of some of the graphite electrodes was accomplished using 10 mL of deoxygenated platinizing solution (0.05 N Pt (IV) in phosphate buffer) with nitrogen blanketing the solution during operation. The potentiostat was set at −931 mV for 2 hours, with the entire system at a forty degree angle to prevent hydrogen gas from building up on the electrode surface. A Ag/AgCl reference electrode was used.

Non-platinized C rods were polished with 0.3 Am alumina for 1 min, then sonicated for 5 min in deionized water. Pt/C rods were not polished.

Next, the films, each formed from a solution having a monomer concentration of 3 Mm (dissolved in phosphate buffer) were formed by electropolymerization onto each electrode surface using cyclic voltammetry, with the potential cycling from 0.00 V to +0.80 V and back to 0.00 V (vs. SCE) at 5 mV/s for ten to twelve scans.

Each of the electrodes was then turned surface-up and treated with a solution of one of the ferrocene compounds (0.05M, in ethanol). Three successive drops (approximately 10 μl each) of the ferrocene solution were applied to the film-covered surface, with each drop being allowed to dry before the next was applied. After the third drop dried, the electrode was rinsed in distilled/deionized water. The following combinations of electrode composition, monomer composition, and ferrocene compound were used:

TABLE IV

| Sensor No. | Base Electrode | Monomer Composition | Ferrocene Compound |
|---|---|---|---|
| 1 | C | 3-Aminophenol | α-HEF |
| 2 | Pt/C | 1,3-DAB | α-HEF |
| 3 | C | 1,3-DAB | α-HEF |
| 4 | Pt/C | 1,3-DAB | 1,1¹-DMF |
| 5 | C | 1,3-DAB | 1,1¹-DMF |

Glucose oxidase (GOX) was then immobilized by crosslinking with glutaraldehyde. A solution containing either 5500 units/ml or 11,000 units/ml of GOX was prepared by dissolving approximately 0.40 g or 0.80 g. GOX (25,000 units/g) in I mL phosphate buffer (0.1 M; pH 6.5). One mL of 25% glutaraldehyde was then added and the solution was mixed. The glutaraldehyde concentration for crosslinking is now 12.5%. (A 1.25% glutaraldehyde solution (950 μL buffer and 50 μL glutaraldehyde) also was used.) The enzyme solution (approximately 20 μL) was placed onto each electrode (inverted) for 0.5 hour.

The experiments were performed in "batch" mode with stirring. Each sensor was placed in 20.00 mL of phosphate buffer together with the SCE reference and Pt mesh auxiliary, the potential applied and the response allowed to come to baseline. The required amount of analyte was added to the solution to measure the response to chosen electroactive interferents (acetaminophen and L-ascorbic acid) and to generate a glucose calibration curve over the desired range.

The order of modification of the electrode surface of film/mediator/enzyme results in an easily and quickly constructed ferrocene-mediated glucose biosensor with excellent linearity and good stability. The construction of these biosensors is very simple. One component is electropolymerized and the other two are adsorbed by the thin polymer film, thus minimizing the time and complexity of construction. Also, we believe this construction method can be applied to any graphite electrode, regardless of shape or size. This capability does not exist in currently used technology.

By using an electron mediator in this system, there is little dependence on oxygen, extending the linearity of response to glucose up to 95 mM. Working at lower potentials decreases background noise. The durability of this sensor appears good, as it remained stable for up to 30 days, while still effectively blocking out interferences.

Miniaturized Biosensor

There is serious need for miniaturized biosensors (e.g., having an electrode sensing surface diameter of about 50 microns or less), especially for in vivo and physiological studies. Results obtained by medical researchers have shown that smaller implanted sensors have greater biocompatibility than larger sensors. A glucose ultramicrobiosensor would have medical applications for neurological studies and blood monitoring. Such a sensor could eventually be used in artificial organs, such as an artificial pancreas, and could be used to treat diabetes.

Platinum Ultramicroelectrodes

We have developed two techniques for the construction of platinum ultramicroelectrodes (diameter=25 micrometers) of the present invention.

Method No. 1

Approximately 1 cm of 25 micrometer diameter platinum wire (AESAR) is placed in one end of a 8 cm length of 4 mm (outer diameter) soda-lime, or soft, glass tubing. It is then heated in the flame of a Bunsen burner, so that the glass melts around the wire. Electrical contact to the platinum wire is made using Wood's metal and a piece of insulated 22 gauge copper wire as a lead wire. The electrode is then polished to a flat surface, with successively finer grades of sandpaper and alumina. The resulting geometry is a microdisk having a diameter of 25 micrometers. Platinum wires of different diameters, e.g., in the range of about 10 to 50 micrometers, can be used to prepare the ultramicroelectrodes of the present invention.

Method No. 2

The exposed end of an insulated 22 gauge copper lead wire is dipped into a container of conductive metal paint, such as nickel print (GC Electronics, Rockford, Ill.). While the paint is wet, an approximately 1 cm piece of 25 micrometer platinum wire is "stuck" to the painted end of the lead wire, and the connection is allowed to air dry (less than 1 hour). When dry, the entire assembly is placed inside a 8 cm length of soft glass tubing, and the end with the platinum wire is capped with a small rubber septum. A disposable syringe, with hypodermic needle, is used to fill the glass tube with Epon 828 epoxy resin (Miller-Stephenson, Danbury, Conn. that has been prepared according to the manufacturer's directions. The electrodes are then placed in a drying oven at 75° C. for two hours, and then at 150° C. for an additional two hours. After allowing the electrodes to cool to room temperature, the rubber septa are removed, and the electrode is polished in the manner described in Method No. 1, above.

It has been our experience, to date, that Method No. 1 is not only simpler to use, but that it has a much higher success rate (50-60%, as opposed to 25-40%), in terms of usable platinum ultramicroelectrodes. Also, the glass-sealed platinum ultramicroelectrodes (Method No. 1) have higher signal-to-noise ratios, and come to baseline quicker, than the epoxy-sealed platinum ultramicroelectrodes.

Carbon Ultramicroelectrodes

A technique has also been developed for the construction of carbon ultramicroelectrodes (diameter=8 micrometers) based upon Method No. 2 above. A 2.5 cm long carbon fiber (diameter=8 =m) is attached to a lead wire (insulated, 22 gauge copper) using conductive paint. The combination of fiber and wire is then placed within a glass tube, the loose end of the carbon fiber protruding from one end, and the loose end of the copper wire extending through the other end of the tube, capped with a rubber septum. The tube is then filled with Epon 828 epoxy resin. The assembly is then baked in an oven as described in Method No. 2, above. The end of the tube with the protruding carbon fiber is then polished flat, so that the resulting electrode is an 8 micrometer diameter carbon microdisk. Carbon fibers of different diameters, e.g., in the range of about 4 to 20 micrometers, can be used to prepare the ultramicroelectrodes of the present invention.

Platinization of Carbon Ultramicroelectrodes

Figure 12:
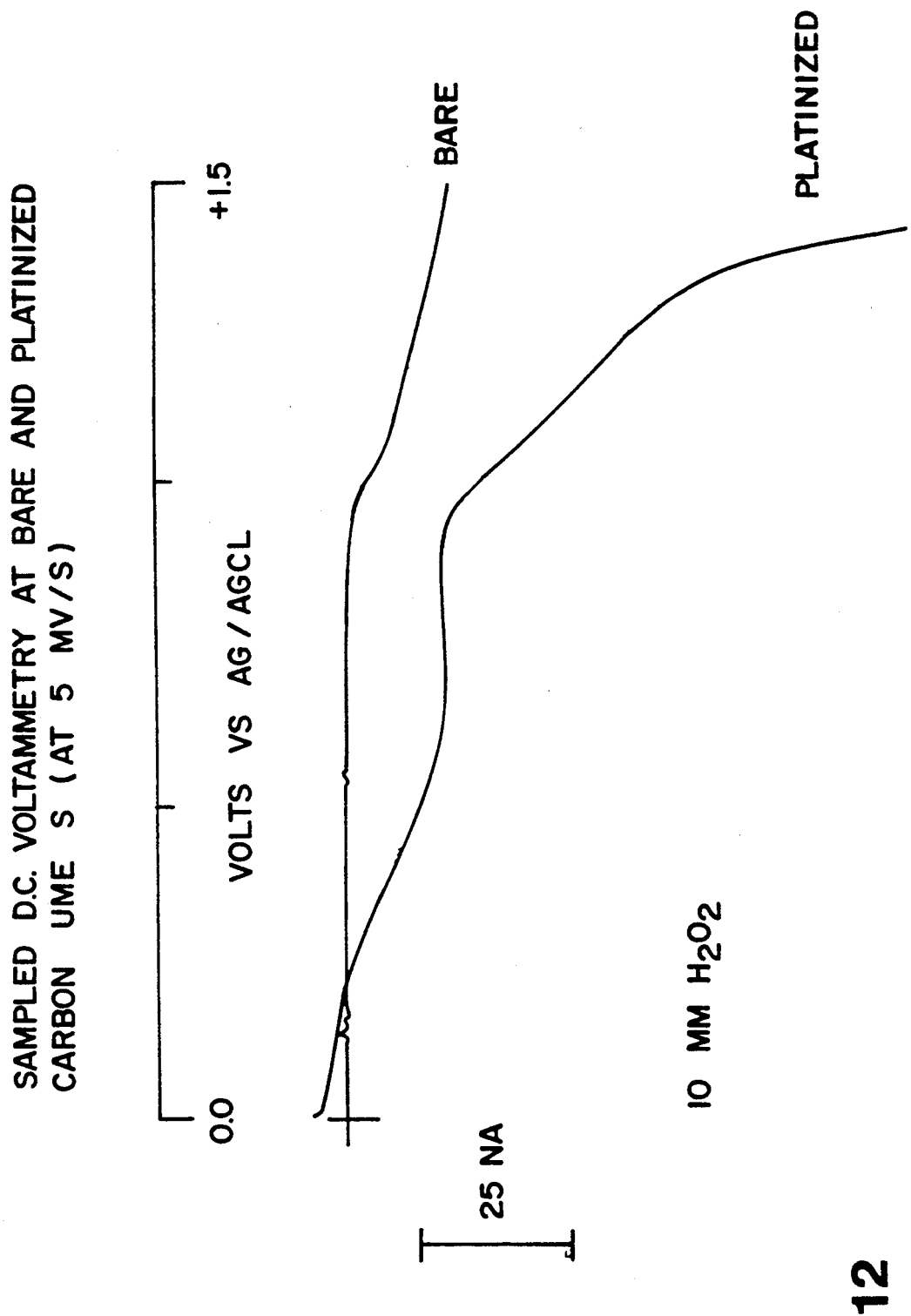
FIG. 12 is a graph of the amperometric responses to hydrogen peroxide at bare and platinized carbon ultramicroelectrodes, using sampled D.C. voltammetry.
Figure 13:
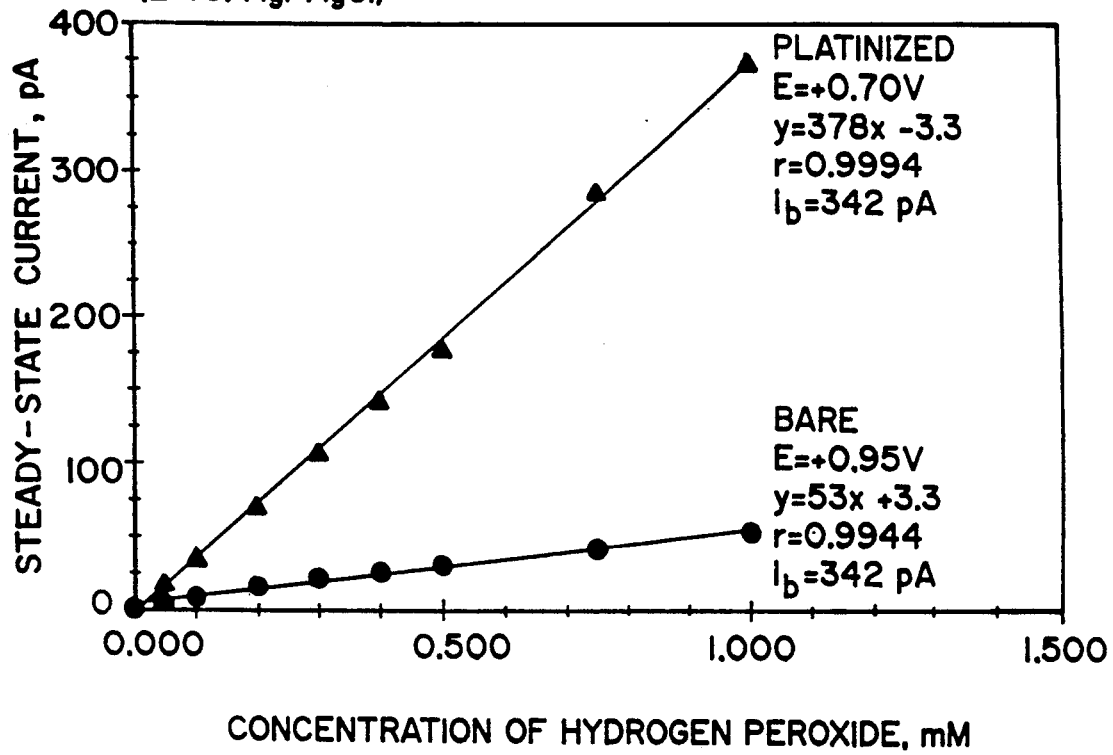
FIG. 13 is a graph relating the concentration of hydrogen peroxide in a phosphate buffer solution contacting an ultramicroelectrode to the amperometric response of the electrode. Data obtained from two different electrodes—one bare carbon, the other platinized carbon—are compared.

Partial platinization of the carbon ultramicroelectrode is used to increase the signal-to-noise ratio for the oxidation of hydrogen peroxide. Sampled D.C. voltammetry was used to characterize the response to hydrogen peroxide at bare and platinized carbon ultramicroelectrodes (see FIG. 12). At a bare carbon ultramicroelectrode (UME), a working potential of at least +0.95V vs. Ag/AgCl is needed to oxidize hydrogen peroxide (in pH 7.4 phosphate buffer). However, at a platinized carbon UME, a lower working potential of +0.70V vs Ag/AgCl is sufficient. The carbon UME was platinized using cyclic voltammetry, $E=0.00V$ to $-0.95V$ vs Ag/AgCl, 20 mV/s, in a solution of $(PtCl_6)^{2-}$. FIG. 13 shows the effect of platinization of a carbon UME on the batch mode response to the oxidation of hydrogen peroxide, in pH=7.4 phosphate buffer. Note that not only is it possible to operate the platinized carbon UME at a lower potential of +0.70V, as opposed to +0.95V, but that the sensitivity to $H_2O_2$ has increased (378 pA/mM, compared to 53 pA/mM), and the background signal has decreased (0.92 pA, compared to 392 pA). The carbon ultramicroelectrodes can also be platinized at a constant potential of $E=-0.95V$ vs Ag/AgCl.

Enzyme Immobilization

The Pt UME's were placed upside down, and a 5 microliter drop of a solution containing 500 mg/ml of glucose oxidase (GOX (EC 1,1,3,4)(12,500 units/mi) in phosphate buffer (0.1 M, pH=6.5) and 1.25% glutaraldehyde was placed on the tip of each electrode and allowed to evaporate. The biosensors were then stored in phosphate buffer at 4° C. overnight.

Electropolymerization of Film

The same film, a copolymer of 1,3-diaminobenzene and resorcinol, is formed in situ by electropolymerization on both the 25 micrometer diameter platinum and the 8 micrometer diameter platinized carbon ultramicroelectrodes.

Ultramicrobiosensors with and without the electropolymerized film, using both types of ultramicroelectrodes (platinized carbon and platinum ultramicroelectrodes), were evaluated.

Figure 14:
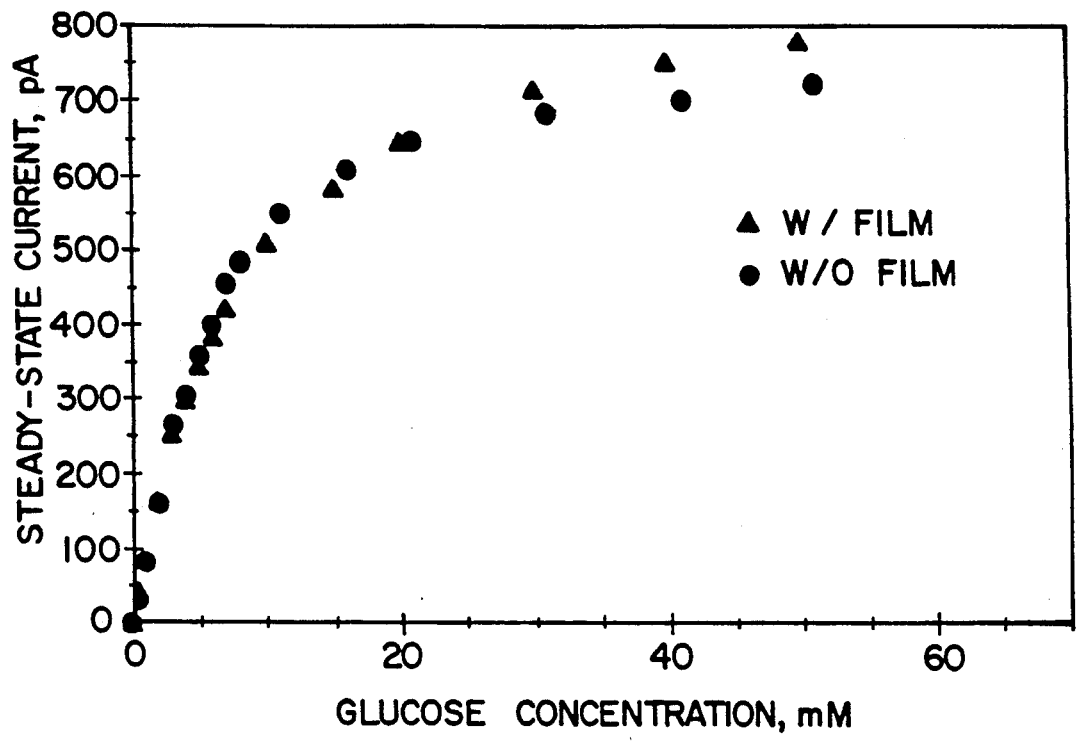
FIG. 14 is a plot of glucose calibration curves for a platinum ultramicrobiosensor of the present invention and the same ultramicroelectrode without a layer of polymer film on the sensing surface.
Figure 15:
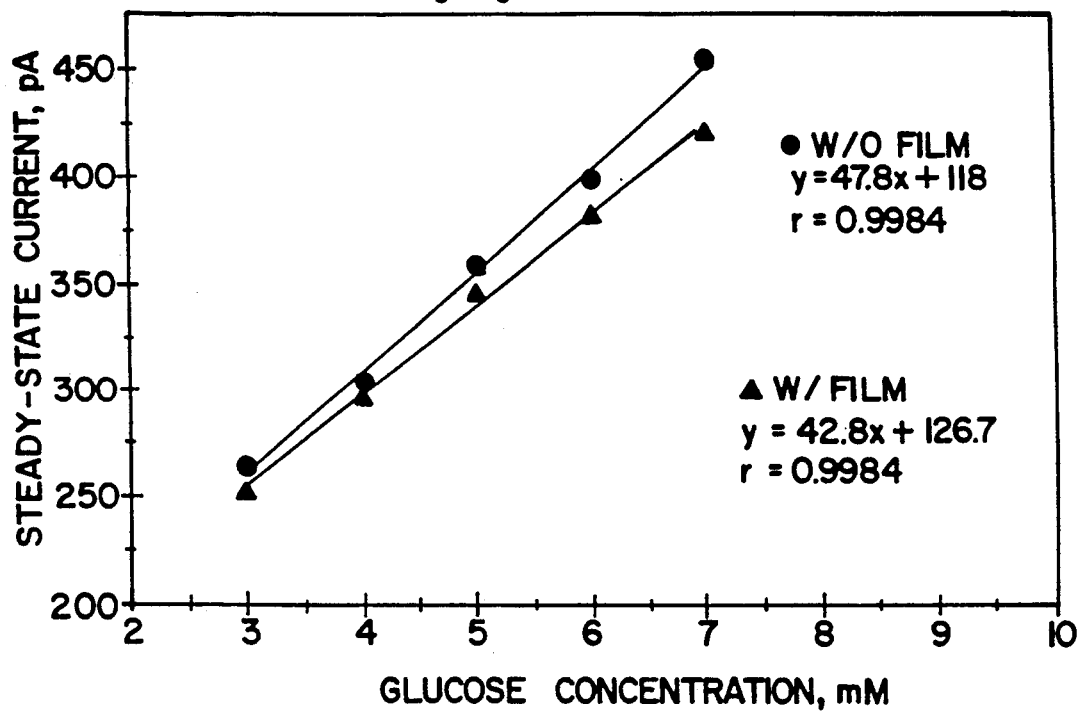
FIG. 15 shows a portion of the same calibration curves as in FIG. 14, an expanded scale, covering only the normal human range of glucose concentration in serum or blood.
Figure 16:
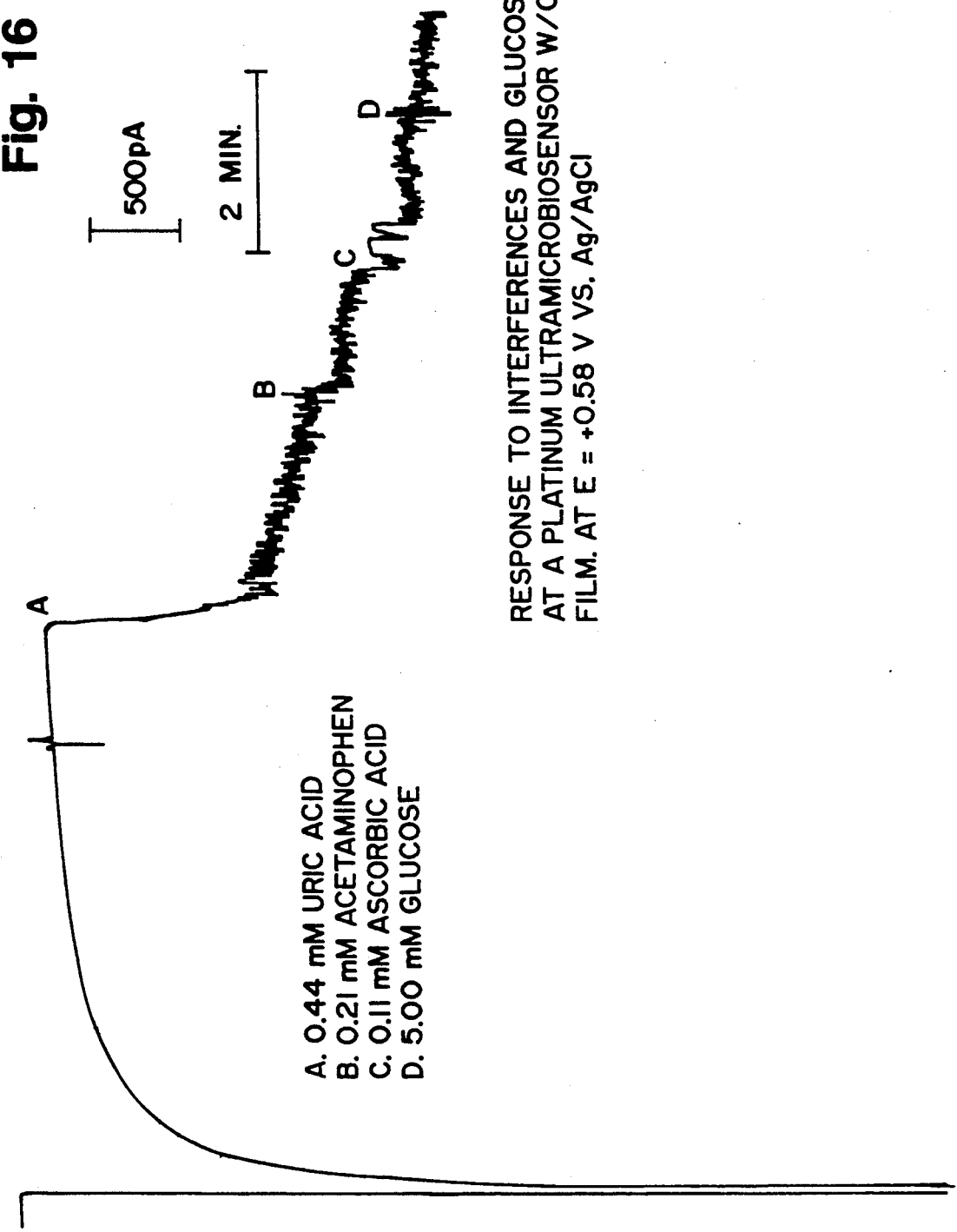
FIG. 16 is a time/amperage plot of current responses at the surface of a platinum ultramicrobiosensor exposed to a biological sample containing glucose and interferents. The sensing surface is coated with immobilized glucose oxidase, but no polymeric film.
Figure 17:
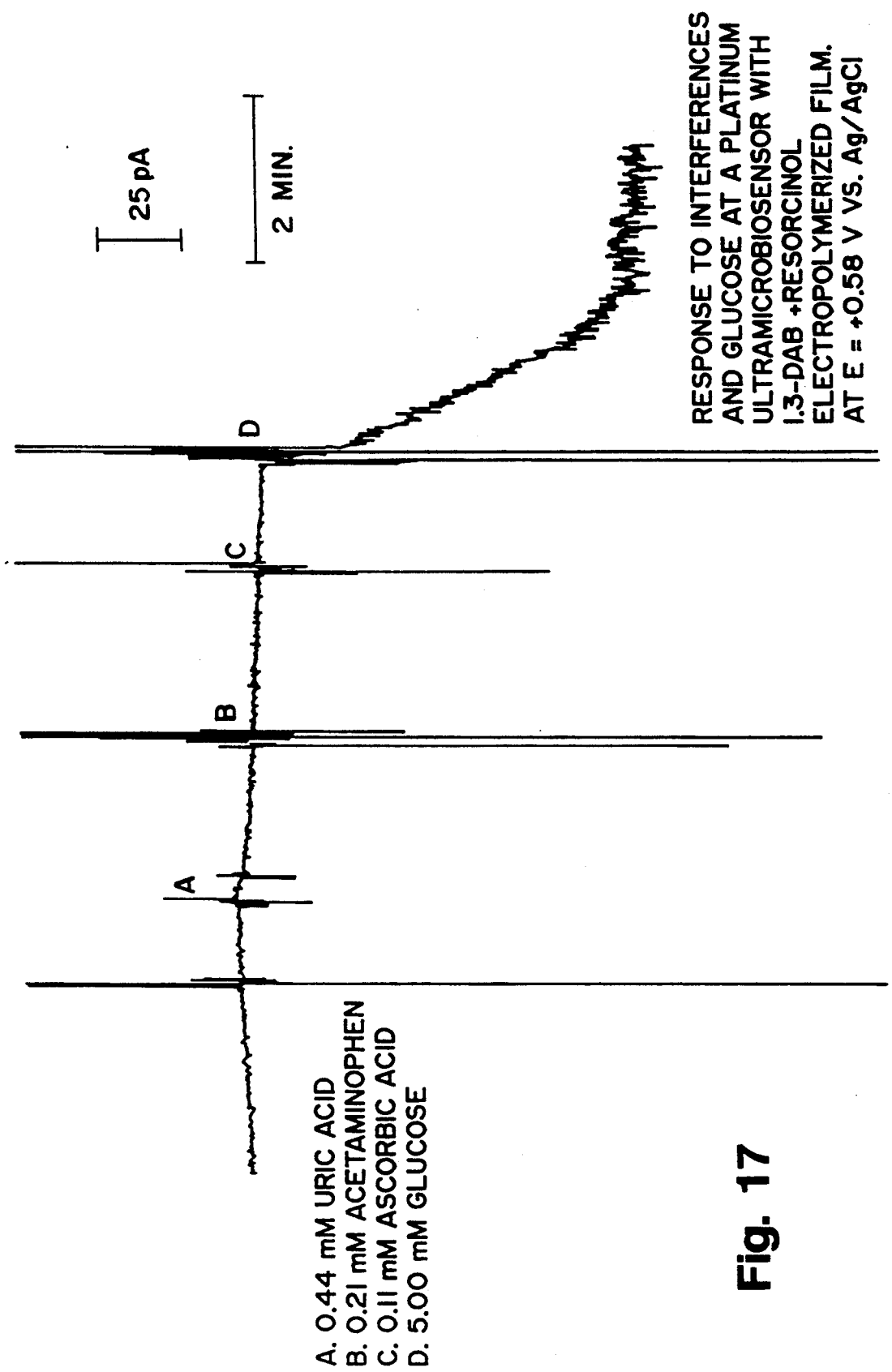
FIG. 17 is a plot of the same time/amperage relationship as shown in FIG. 16, but using an electrode that is coated according to the present invention.

FIG. 14 depicts glucose calibration curves at a platinum ultramicrobiosensor (UMB) with and without the electropolymerized film, at $E=+0.58$ V vs Ag/AgCl (in pH 7.4 phosphate buffer). FIG. 15 shows the same calibration curves expanded to show only the normal human range. Typical batch mode response of a platinum UMB, with no film, is shown in FIG. 16. Note that the baseline is established quickly. The UMB is tested for the three most common interferents present in human serum: uric acid, acetaminophen, and ascorbic acid, in maximum clinical amounts. The total response to the interferences is much larger than that to a normal glucose concentration, 5 mM. FIG. 17 shows the same experiment, run on the same UMB, except that the 1,3-DAB/Res film is present. There is virtually no response to the same three interferences, while the signal for 5 Mm glucose is comparatively large.

Figure 18:
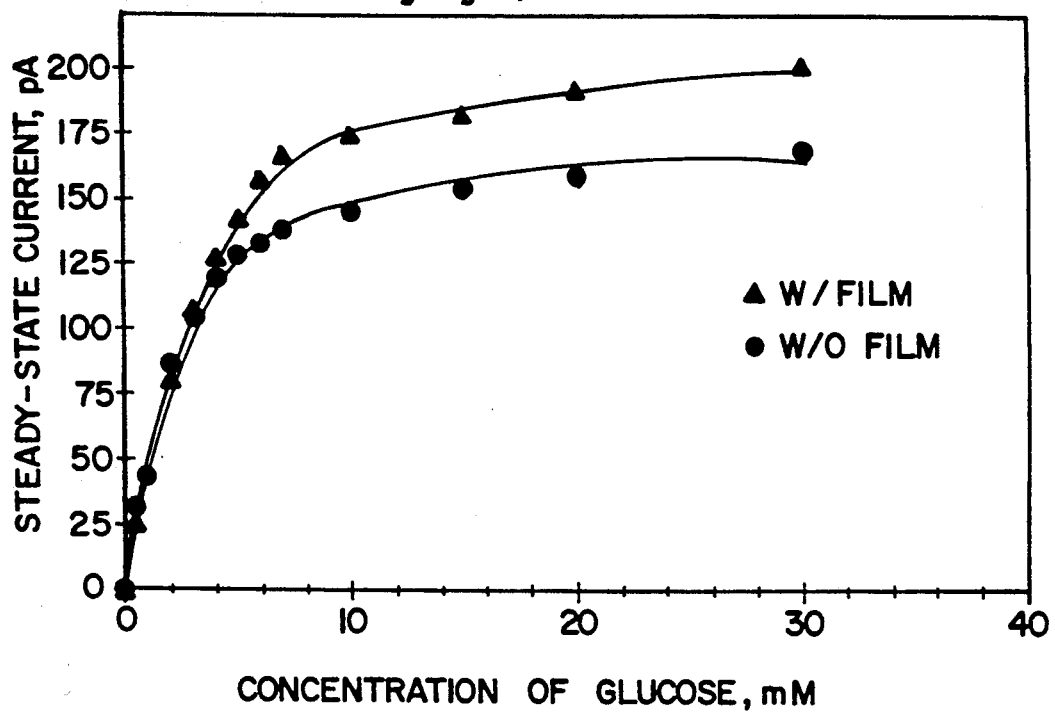
FIG. 18 is a plot of calibration curves similar to those shown in FIG. 14, but using a platinized carbon electrode, rather than a pure platinum electrode.
Figure 19:
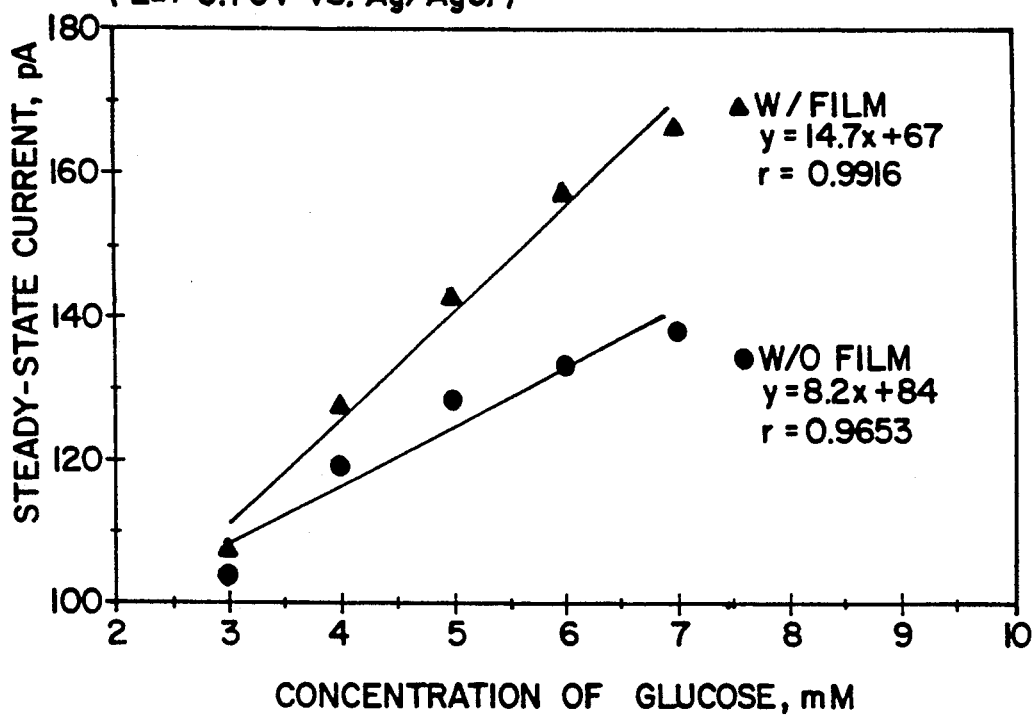
FIG. 19 depicts the same curves as FIG. 18, but on an enlarged scale and over only the normal human range.
Figure 20:
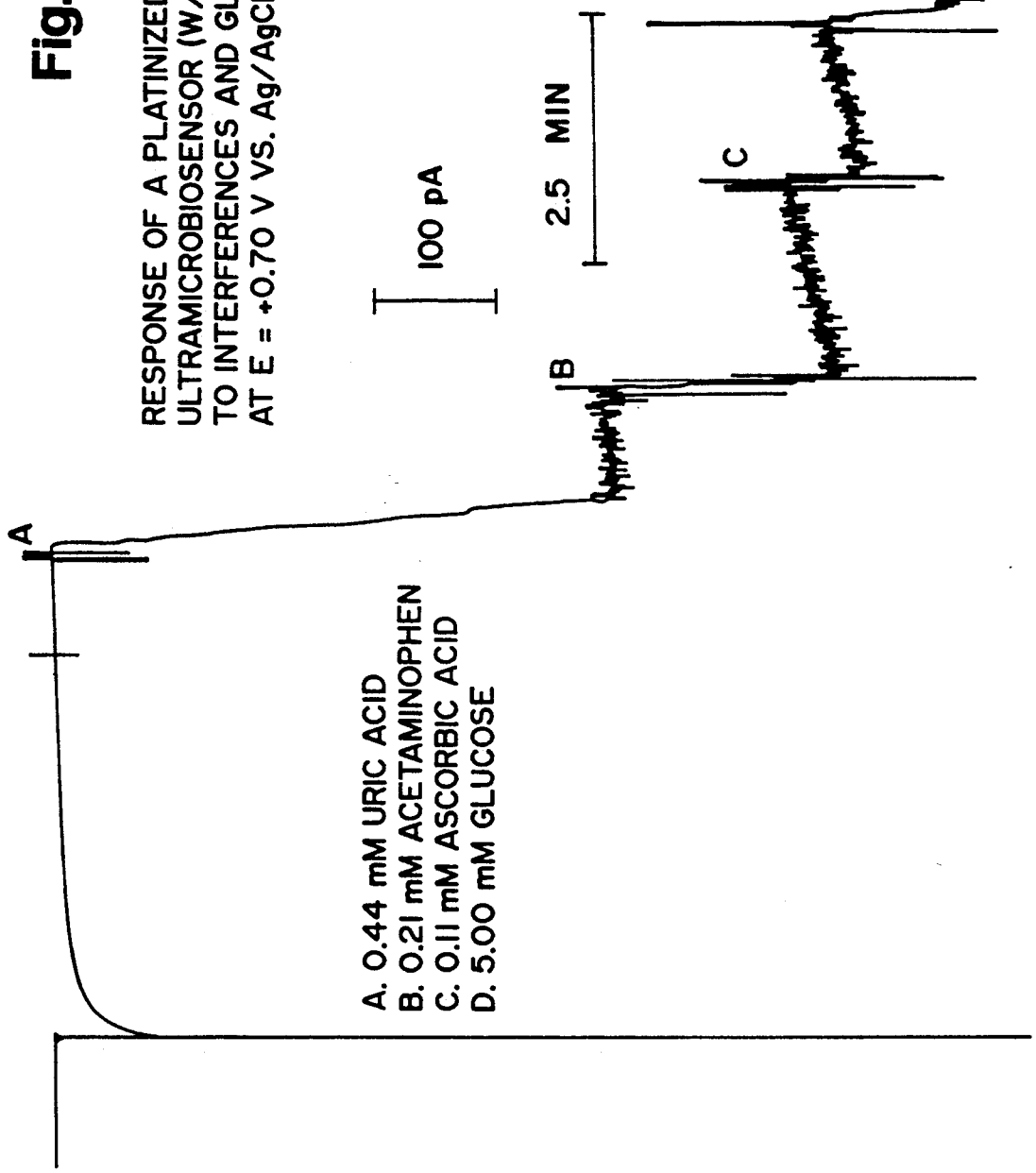
FIG. 20 is a plot of the amperage/time responses of the platinized carbon ultramicrobiosensor without a polymeric coating.
Figure 21:
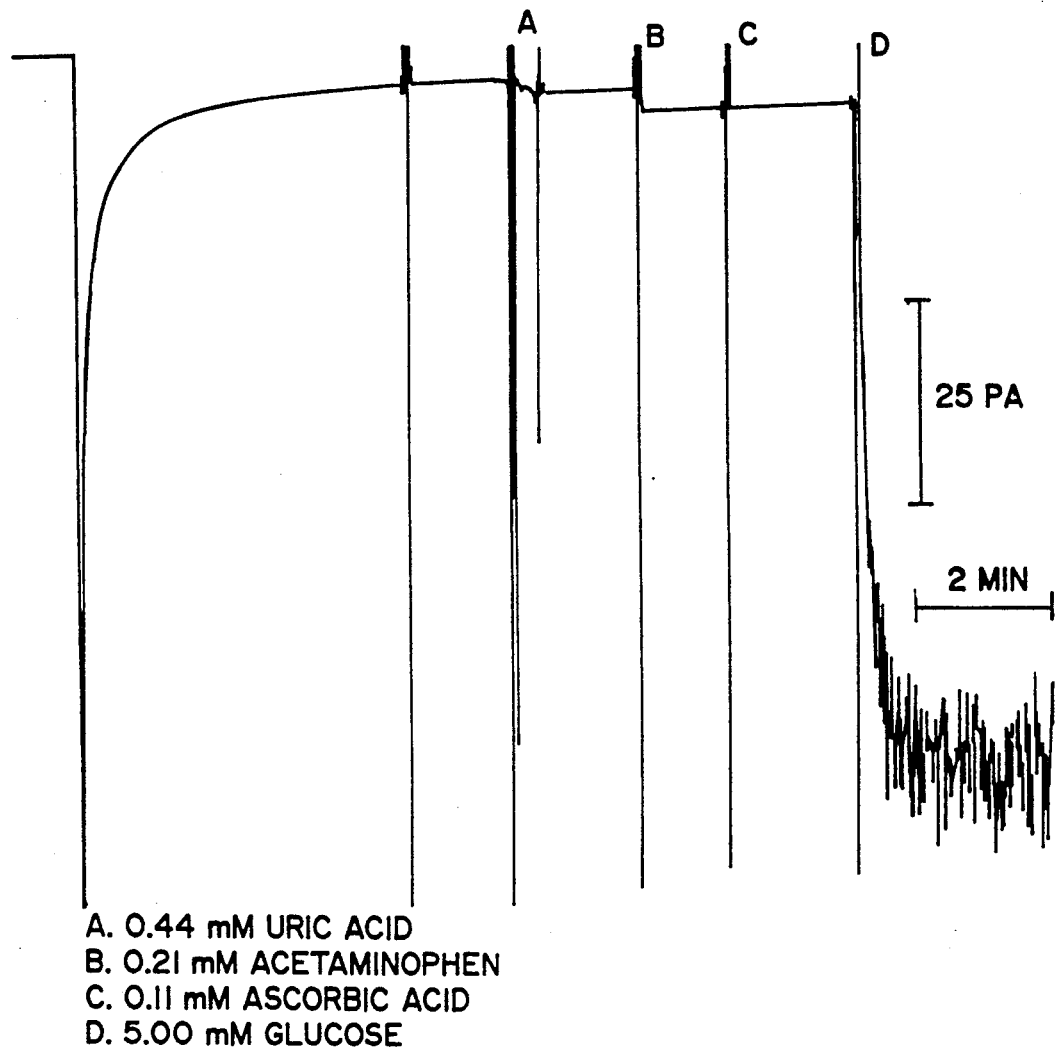
FIG. 21 is a plot of the amperage/time response data for a platinized carbon ultramicrobiosensor provided with a polymer coating according to the present invention.

Calibration curves for glucose at the platinized carbon UMB, with and without the electropolymerized film, are shown in FIG. 18. FIG. 19 depicts the same curves over the normal human range only. The typical batch mode response of a platinized carbon UMB is shown in FIG. 20. Again, note that the sensor establishes baseline quickly. The responses to the three interferences are larger than the signal for 5 mM glucose. However, in FIG. 21, the electropolymerized film can be used to effectively prevent the signals due to the three interferences, while allowing glucose to give a comparatively large response.

In addition to individual wires or fibers, bundles of such can be used, with the wires or fibers isolated one from the other by a matrix of a resin, e.g., an epoxy resin. While not as small in size, the advantage of such electrodes (known as "array electrodes") is that they provide more current than an ultramicroelectrode, while giving a better signal-to-noise ratio than a large single electrode of the same size.

With the benefit of the biosensor embodiments disclosed herein, various modifications and substitutions will now be apparent to persons skilled in the art. Accordingly, the invention is not to be limited to the illustrative embodiments disclosed herein, but is defined by the appended claims.

What is claimed is:

1. A method of making a sensing element for use in a biosensor that amperometrically measures the concentration of an analyte in a biological liquid, said method comprising the following steps:
    a) obtaining a first electrode having a sensing surface;
    b) immersing said sensing surface of said first electrode in a solution of monomer wherein said monomer is electropolymerizable into an electrically non-conducting polymer;
    c) flowing an electric current from a cathode, through said solution, to said first electrode, at a voltage and amperage sufficient to cause the monomer to be electropolymerized on the sensing surface of the first electrode;
    d) ceasing the current flow after the amperage of the current as measured at the first electrode declines to a relatively steady minimum, thereby yielding a sensing surface coated with an adherent layer of electrically non-conducting polymer;
    e) disposing with the polymeric coating on the sensing surface of the first electrode a chemical sensing agent that, when contacted by a specific analyte in a biological liquid, generates an electroactive molecule that can be detected amperometrically.

2. A method of making a sensing element for use in a biosensor that amperometrically measures the concentration of an analyte in a biological liquid, said method comprising the following steps:
    a) obtaining a first electrode having a sensing surface;
    b) applying to said sensing surface of said first electrode a chemical sensing agent that, when contacted by a specific analyte in a biological liquid, generates an electroactive molecule that can be detected amperometrically.
    c) immersing said sensing surface of said first electrode in a solution of monomer wherein said monomer is electropolymerizable into an electrically non-conducting polymer;
    d) flowing an electric current from a cathode, through said solution, to said first electrode, at a voltage and amperage sufficient to cause the monomer to be electropolymerized on the sensing surface of the first electrode; and
    e) ceasing the current flow after the amperage of the current as measured at the first electrode declines to a relatively steady minimum, thereby yielding a sensing surface coated with an adherent layer of electrically non-conducting polymer having said chemical sensing agent disposed therewith.

3. A method according to claim 1 comprising ceasing the current flow when a stable polymer film is formed.

4. A method according to claim 1 comprising embedding said chemical sensing agent in said electrically non-conducting polymer during electropolymerization.

5. A method according to claim 1 comprising entrapping said chemical sensing agent in said electrically non-conducting polymer during electropolymerization.

6. A method according to claim 1 comprising disposing said chemical sensing agent on said layer of electrically non-conducting polymer during electropolymerization.

7. A method according to claim 2 comprising ceasing the current flow when a stable polymer film is formed.

8. A method according to claim 2 comprising embedding said chemical sensing agent in said electrically non-conducting polymer during electropolymerization.

9. A method according to claim 2 comprising entrapping said chemical sensing agent in said electrically non-conducting polymer during electropolymerization.

10. A method according to claim 2 comprising disposing said chemical sensing agent on said layer of electrically non-conducting polymer during electropolymerization.

11. A method of making a sensing element for use in a biosensor for amperometrically measuring the concentration of an analyte in a biological liquid, said method comprising:
    a) obtaining an electrode having a sensing surface;
    b) applying a layer of electrically non-conducting polymer attached to and covering the sensing surface of said electrode by forming said polymer by electropolymerizing a monomer directly onto said sensing surface by using said electrode as a working electrode to conduct the electric current driving the polymerization, said polymer layer being sufficiently solid to shield the electrode surface from contact with interferents in a biological liquid when the sensing element is immersed therein;
    c) disposing a chemical sensing agent partially embedded in said layer of polymer, said sensing agent having analyte recognition sites that are not blocked by said polymer, said sites being operable, when contacted by a specific analyte in a biological liquid sample, to generate an electroactive molecule that can be detected amperometrically if it reaches the sensing surface of the electrode;
    d) permeating said polymer layer by diffusing said electroactive molecule through said polymer layer to contact the sensing surface of the electrode.

* * * * *